(12) United States Patent
Huang

(10) Patent No.: US 10,596,169 B2
(45) Date of Patent: Mar. 24, 2020

(54) CANCER TREATMENT WITH COMBINATION OF PLINABULIN AND TAXANE

(71) Applicant: BeyondSpring Inc., Camana Bay, Grand Cayman (KY)

(72) Inventor: Lan Huang, Bronx, NY (US)

(73) Assignee: BeyondSpring Inc., Camana Bay (KY)

( * ) Notice: Subject to any disclaimer, the term of this patent is extended or adjusted under 35 U.S.C. 154(b) by 0 days.

(21) Appl. No.: 15/028,376

(22) PCT Filed: Oct. 11, 2013

(86) PCT No.: PCT/CN2013/085075
§ 371 (c)(1),
(2) Date: Apr. 8, 2016

(87) PCT Pub. No.: WO2015/051543
PCT Pub. Date: Apr. 16, 2015

(65) Prior Publication Data
US 2016/0250209 A1    Sep. 1, 2016

(51) Int. Cl.
*A61K 31/496* (2006.01)
*A61K 31/337* (2006.01)

(52) U.S. Cl.
CPC .......... *A61K 31/496* (2013.01); *A61K 31/337* (2013.01)

(58) Field of Classification Search
CPC .................................................. A61K 31/496
USPC .................................................. 514/254.05
See application file for complete search history.

(56) References Cited

U.S. PATENT DOCUMENTS

| | | | |
|---|---|---|---|
| 7,629,380 B2 | 12/2009 | McMorris et al. | |
| 7,700,615 B2 | 4/2010 | Edwards et al. | |
| 7,919,497 B2 | 4/2011 | Palladino et al. | |
| 7,956,058 B2 | 6/2011 | Hayashi | |

FOREIGN PATENT DOCUMENTS

| WO | WO 2004/054498 | 11/2004 |
|---|---|---|
| WO | WO 2005/077940 | 8/2005 |
| WO | WO 2014160183 | 10/2014 |

OTHER PUBLICATIONS

Mita et al., "Phase II study of docetaxel with or without plinabulin (NPI-2358) in patients with non-small cell lung cancer (NSCLC)", J.Clin.Oncol., 2010, vol. 28, No. 15 supplement, p. 7592 (Year: 2010).*
Perez, Oncologist, 1998, vol. 3, pp. 373-389 (Year: 1998).*
Paik et al., Cancer Chemother. Pharmacol., 2011, vol. 68, No. 5, pp. 1331-1337 (Year: 2011).*
Michael Milward et al., "Phase 1 study of the novel vascular disrupting agent plinabulin (NPI-2358) and docetaxel," The Journal of New Anticancer Agents, vol. 3, No. 30, Feb. 16, 2011.
International Search Report for International Application No. PCT/CN2013/085075 dated Jul. 16, 2014 by State Intellectual Property Office of the P.R. China.
Written Opinion for International Application No. PCT/CN2013/085075 dated Jul. 16, 2014 by State Intellectual Property Office of the P.R. China.
Ji et al., Tubulin Colchicine Binding Site Inhibitors as Vascular Disrupting Agents in Clinical Developments, Current Medicinal Chemistry (2015), 22(11), 1348-1360.
Hayashi et al., Medicinal chemistry and chemical biology of diketopiperazine-type antimicrotubule and vascular-disrupting agents, Chemical & Pharmaceutical Bulletin (2013), 61(9), 889-901.
Bankowska et al., Derivatives of 1,2,3-triazole. Potential drugs?, Wiadomosci Chemiczne (2012), 66(11-12), 993-1022.
Cai, Small molecule vascular disrupting agents: potential new drugs for cancer treatment, a 2009 update, Frontiers in Anti-Cancer Drug Discovery (2010), 1, 380-427.
Petrillo et al., Novel VEGF-independent strategies targeting tumor vasculature: clinical aspects, Current Pharmaceutical Design (2012), 18(19), 2702-2712.
Yamazaki et al., Drug discovery study on cyclic dipeptides anti-cancer drugs and chemical biological development, Idenshi Igaku Mook (2012), 21(Saishin Pepuchido Gosei Gijutsu to Sono Soyaku Kenkyu eno Oyo), 260-266.
Millward et al., Phase 1 study of the novel vascular disrupting agent plinabulin (NPI-2358) and docetaxel, Investigational New Drugs (2012), 30(3), 1065-1073.
Aggarwal et al., Antiangiogenic agents in the management of non-small cell lung cancer: Where do we stand now and where are we headed? Cancer Biology & Therapy (2012), 13(5), 247-263.
Spear et al., Vascular disrupting agents (VDA) in oncology: advancing towards new therapeutic paradigms in the clinic, Current Drug Targets (2011), 12(14), 2009-2015.
Bertelsen et al., Vascular effects of plinabulin (NPI-2358) and the influence on tumour response when given alone or combined with radiation, International Journal of Radiation Biology (2011),87(11), 1126-1134.
Singh et al., A novel vascular disrupting agent plinabulin triggers JNK-mediated apoptosis and inhibits angiogenesis in multiple myeloma cells, Blood (2011), 117(21), 5692-5700.

(Continued)

Primary Examiner — Jeffrey S Lundgren
Assistant Examiner — Stephanie K Springer
(74) Attorney, Agent, or Firm — Knobbe, Martens, Olson & Bear, LLP

(57) ABSTRACT

This invention provides a novel cancer treatment method in which plinabulin (t-butyl-dehydrophenylahistin or NPI-2358) and a taxane compound (such as docetaxel) are used in combination. Our study has shown that the optimum combination of injecting plinabulin after taxane compound has unexpected enhanced efficacy in large tumor populations in animal model and in NSCLC cancer patients compared to taxane compound treatment alone. In addition, this optimum combination can achieve unexpected safety effect in lowering unbearable side effects of taxane compound, including decreasing its neutropenia rates at all grades and decreasing G-CSF use in cancer patients.

6 Claims, 4 Drawing Sheets

(56) References Cited

OTHER PUBLICATIONS

Kingston, Tubulin-interactive natural products as anticancer agents, Journal of Natural Products (2011), 74(5), 1352.

Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.

Mita et al., Phase 1 First-in-Human Trial of the Vascular Disrupting Agent Plinabulin(NPI-2358) in Patients with Solid Tumors or Lymphomas, Clinical Cancer Research (2010), 16(23), 5892-5899.

Mita et al., Randomized Phase 2 Study of Docetaxel +/− Plinabulin (NPI-2358) in Patients with Non-Small Cell Lung Cancer (NSCLC) Mol Cancer Ther 8 Suppl. (Abstr C30) (2009) 2 pages.

Mita et al., Randomized Phase 2 Study of Docetaxel +/− Plinabulin (NPI-2358) in Patients with Non-Small Cell Lung Cancer (NSCLC), Poster Presentation at ACS Annual '10 Meeting (Jun. 4-8, 2010) 1 page.

Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.

Ferrer et al., Plinabulin: tubulin polymerization inhibitor vascular-disrupting agent oncolytic, Drugs of the Future (2010), 35(1), 11-15.

Gridelli et al., Vascular disrupting agents: a novel mechanism of action in the battle against non-small cell lung cancer, Oncologist (2009), 14(6), 612-620.

Kanthou et al., Microtubule depolymerizing vascular disrupting agents: novel therapeutic agents for oncology and other pathologies, International Journal of Experimental Pathology(2009), 90(3), 284-294.

Hayashi et al., Small peptide-based medicinal chemistry for intractable disease, Peptide Science (2009), Volume Date 2008, 45th, 139-140.

Kingston, Tubulin-Interactive Natural Products as Anticancer Agents, Journal of Natural Products (2009), 72(3), 507-515.

Lee et al., Colchicine site inhibitors of microtubule integrity as vascular disrupting agents, Drug Development Research (2008), 69(6), 352-358.

Tozer et al., Tumour vascular disrupting agents: combating treatment Resistance, British Journal of Radiology (2008), 81(Spec. Iss. 1), S12-S20.

Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.

Hayakawa, Structure-activity relationship analysis, Gan to Kagaku Ryoho (2004), 31(4), 526-528.

\* cited by examiner

CANCER TREATMENT WITH COMBINATION OF PLINABULIN AND TAXANE

CROSS-REFERENCE TO RELATED APPLICATIONS

This application is a national phase application of International Application No. PCT/CN2013/085075 (published as WO 2015/051543), filed Oct. 11, 2013, entitled "CANCER TREATMENT WITH COMBINATION OF PLINABULIN AND TAXANE," which is incorporated by reference herein in their entirety and for all purposes.

TECHNICAL FIELD

The present invention relates to medical field and in particular to a method of treating cancer using a combination of Plinabulin and taxane in treating cancer patients, and its unexpected effect in dramatically increasing taxane's safety and dramatically decreasing taxane's side effects, and its unexpected efficacy effect in large tumor in animal model and cancer patients.

BACKGROUND ART

Cancer has overtaken cardiovascular diseases as the leading cause of disease incurred death in the world. In the US over 1 million people get cancer each year, while in China, over 3 million people get cancer each year. 45% of new cancer cases in the world occur in China. The most widely used treatment for cancer is chemotherapy agents, such as taxanes. However, due to taxane's unbearable side effects, including high neutropenia rates (grade 3-4 at 30-40%), its dose has to be decreased during the use or even its use has to be terminated, and thus lowering down its efficacy and treatment duration in cancer patients.

Lung cancer is the leading cause of cancer-related mortality in the United States, China, and the world. Non-small cell lung cancer (NSCLC) accounts for approximately 80% of all cases of lung cancer. By the time most patients are diagnosed with NSCLC, the disease is already advanced. Standard approved therapies for advanced NSCLC generally include successive lines of chemotherapy agents including platins, taxanes, vinca alkyloids, pemetrexed, and/or epidermal growth factor receptor (EGFR) inhibitors.

Docetaxel is a taxane compound approved as second line treatment of NSCLC in the US, European Union, China and multiple other countries. Docetaxel functions by disrupting the microtubule network in cells. It is generally administered as a 1-hour intravenous (IV) infusion once every 3 weeks at a dose of 75 mg/m$^2$ with dexamethasone premedication to minimize the probability of hypersensitivity reactions and fluid retention. In 2 randomized trials with docetaxel in patients with NSCLC previously treated with a platinum-based chemotherapy regimen, the median overall survival (OS) ranged from 5.7 to 7.5 months.

The most common adverse reactions with docetaxel include infections, neutropenia, anemia, febrile neutropenia, hypersensitivity, thrombocytopenia, and etc. Several additional chemotherapeutic agents have been approved as second line therapies for Stage IIIb/IV NSCLC (pemetrexed, erlotinib, and gefitinib), but have clinically equivalent OS outcomes. In wide type NSCLC patients (stage IIIb/IV, second line), OS for docetaxel cohort (75 mg/m$^2$) was 8.2 M, much longer than OS of some other drugs. Thus docetaxel is still the treatment of choice in second line NSCLC treatment.

Since the treatment of cancers is still unsatisfied, there is a clear unmet medical need for additional anti-cancer agents in cancer patients such as those with advanced NSCLC.

SUMMARY OF THE INVENTION

The object of the invention is to provide an optimum method to treat cancer.

Another object of the present invention is to provide the corresponding combination of medicine, a kit and their use for treatment and/or prevention of cancer especially lung cancer.

In the first aspect of the invention, it is provided a pharmaceutical combination comprising an active ingredient (a) of a taxane compound; and an active ingredient (b) of plinabulin.

In a preferred embodiment, the taxane compound comprises paclitaxel, docetaxel, and abraxane.

In a preferred embodiment, the combination consists of docetaxel and plinabulin.

In the second aspect of the invention, it is provided a use of the pharmaceutical combination in the first aspect for preparing drugs for treating and/or preventing cancer.

In a preferred embodiment, the cancer selected from the group consisting of lung cancer, colon cancer, liver cancer, breast cancer, prostate cancer, and multiple myeloma.

In the third aspect of the invention, it is provided a use of a composition, a kit or a mixture comprising an active ingredient (a) of taxane and an active ingredient (b) of plinabulin for treating and/or preventing cancer.

In one preferred embodiment, the cancer has a tumor size of >3 cm, >5 cm, or >7 cm.

In the 4th aspect of the invention, it is provided a kit which contains (i) a first container containing a first medicament which comprises a taxane compound as an active ingredient (a) and an optional pharmaceutically acceptable carrier; and (ii) a second container containing a second medicament which comprises plinabulin as an active ingredient (b) and an optional pharmaceutically acceptable carrier;

(iii) an optional instruction recording an administration of the active ingredient (a) in combination with the active ingredient (b) for treating and/or preventing cancer.

Preferably, the instruction indicates that plinabulin has to be injected 1-24 hours after administrating taxane.

Preferably, there are 8 first medicament at 20 mg per vial and 2 second medicament at 80 mg per vial in a single kit.

In the 5th aspect of the invention, it is provided a pharmaceutical composition, wherein it comprises:

an active ingredient (a) of taxane;

an active ingredient (b) of plinabulin; and (c) a pharmaceutical acceptable carrier.

In one preferred embodiment, the ratio (mg:mg) of active ingredient (a) to active ingredient (b) is 1:100 to 50:1; preferably, 1.5:1 to 4:1.

In one preferred embodiment, the total amount of the active ingredient (a) and the active ingredient (b) is 1-99 wt %; and more preferably, 5-90 wt % of the composition.

In the 6th aspect of the invention, it is provided a use of plinabulin for preparation of a medicine used to reduce side effect of taxane.

In one preferred embodiment, the side effect comprises neutropenia, anemia, febrile neutropenia, thrombocytopenia.

In the 7th aspect of the invention, it is provided a method for reducing side effect of taxane, wherein it comprises a step of administrating plinabulin to the subject in need prior to, at same time or after administrating a taxane compound.

In the 8th aspect of the invention, it is provided a method for treating and/or preventing cancer, comprising the following steps: administrating to a mammal in need thereof an active ingredient (a) of taxane and an active ingredient (b) of plinabulin Preferably, administrating the active ingredient (a) first and then administrating and the active ingredient (b).

In the 9th aspect of the invention, it is provided a method of use of plinabulin and docetaxel combination for treating cancer in a subject in that plinabulin has to be injected after docetaxel for the enhanced efficacy to treat cancer in the range of 1-24 hours after.

In one preferred embodiment, the subject is a patient of large tumor in various cancer types.

In one preferred embodiment, the subject is a patient of stage IIIb/IV NSCLC having at least one lung primary tumor >3 cm, preferably >5 cm, and more preferably >7 cm.

In the 10th aspect of the invention, it is provided a method of use in taxanes combined with plinabulin to decrease the toxicity in taxanes, especially its grade 3 and 4 neutropenia.

It is provided a method of use of plinabulin and docetaxel in NSCLC patient treatment in decreasing of docetaxel's neutropenia rate at all grades, and decreasing G-CSF use.

It should be understood that, in the present invention, the technical features specifically described above and below (such as in the Examples) can be combined with each other, thereby constituting new or preferred technical solutions, which need not be specified herein.

DESCRIPTION OF FIGURES OF THE INVENTION

Figure 3:
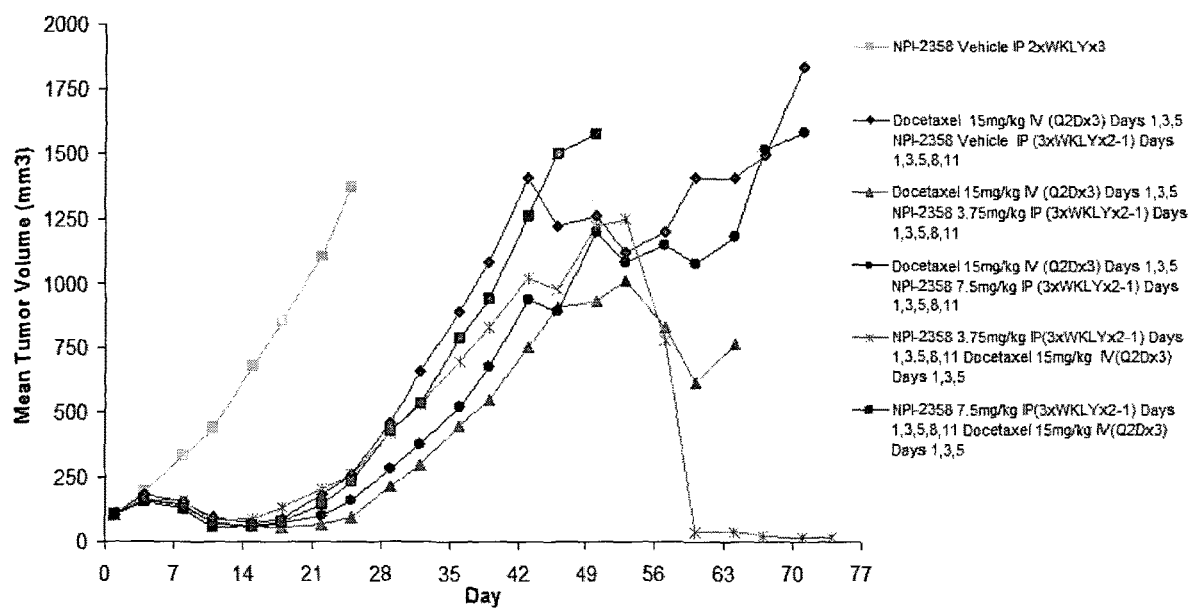

FIG. 3 shows mean tumor volume in Example 1 (NSCLC MV522 tumor model). The addition of Plinabulin (NPI-2358) enhanced the antitumor activity of docetaxel. The synergistic effect was more prominent in the groups receiving docetaxel first followed by NPI-2358 2 hours later.

Figure 4A:
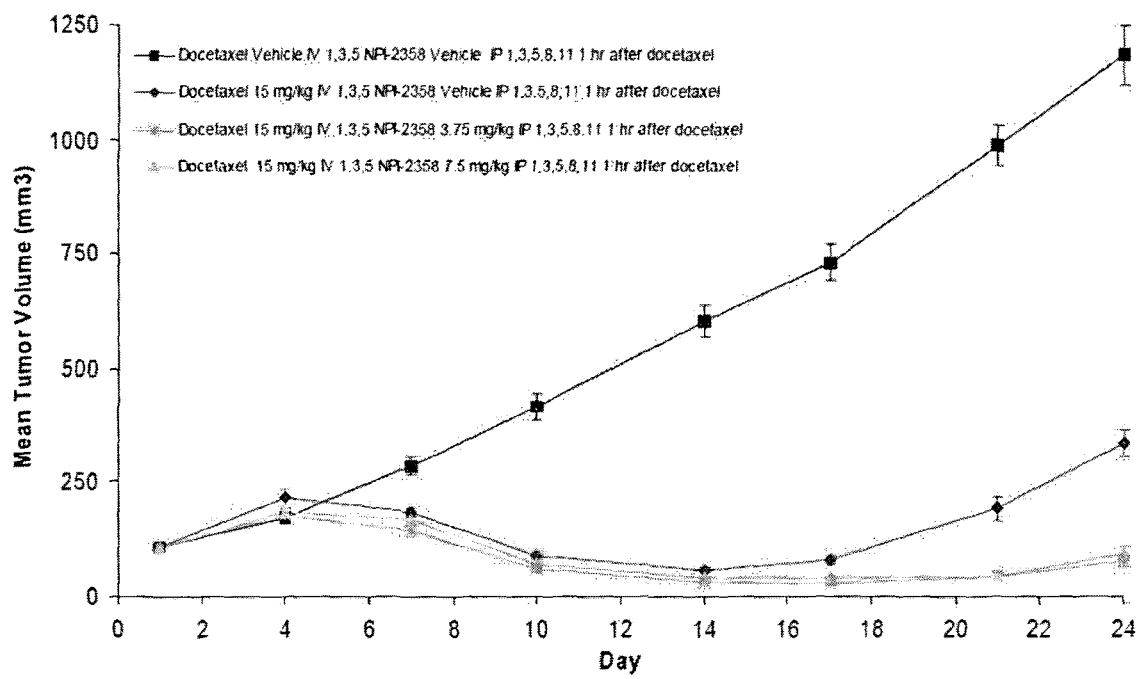
Figure 4B:
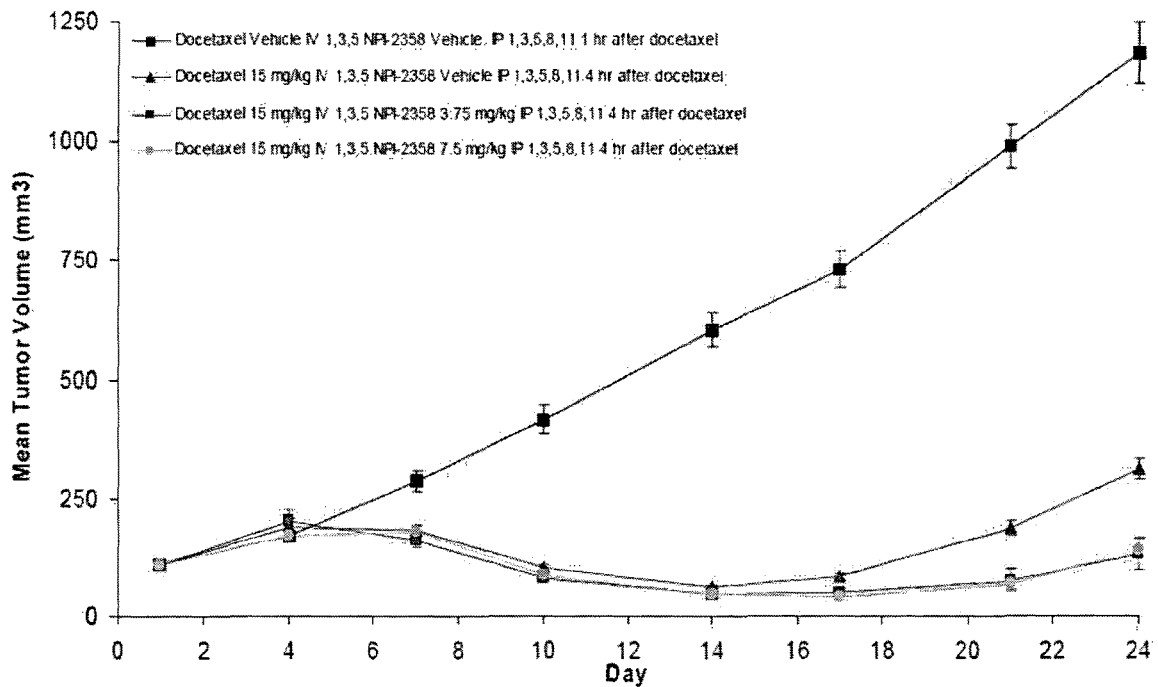
Figure 4C:
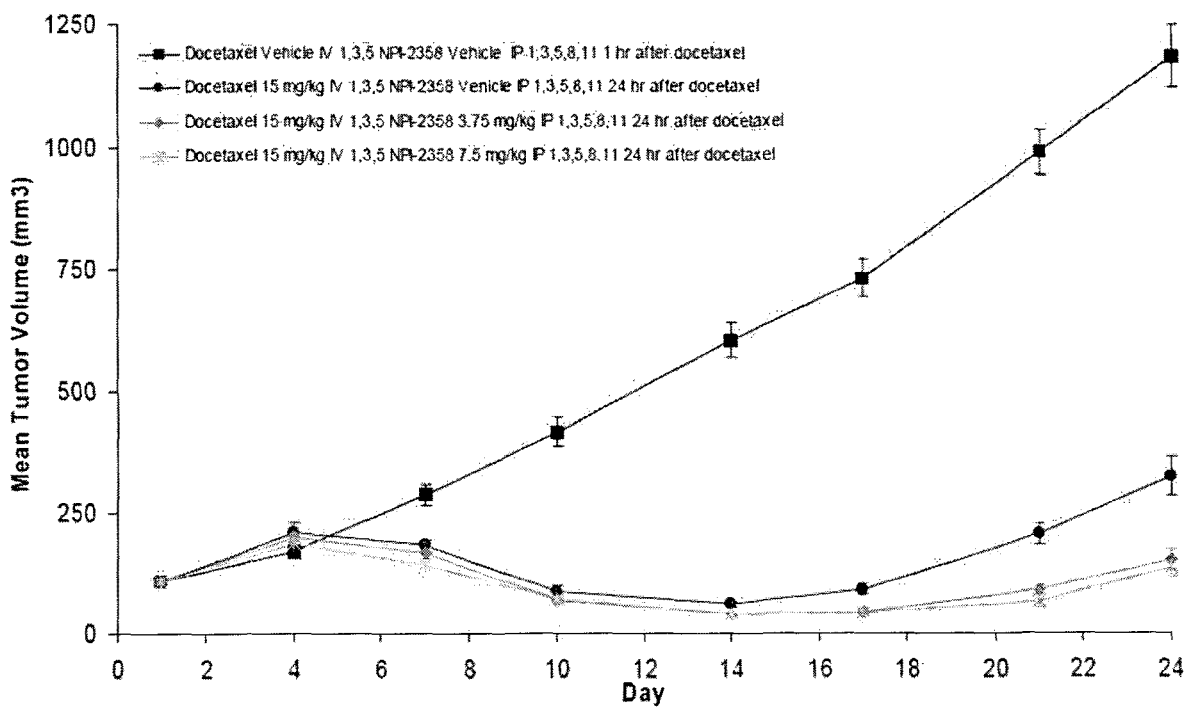

FIG. 4A, FIG. 4B and FIG. 4C show mean tumor volume in Example 2 (NSCLC MV522 tumor model). The antitumor activity enhancement effect of Plinabulin (NPI-2358) added to docetaxel were similar in groups receiving docetaxel first followed by plinabulin 1, 4, or 24 hours later.

Figure 5:
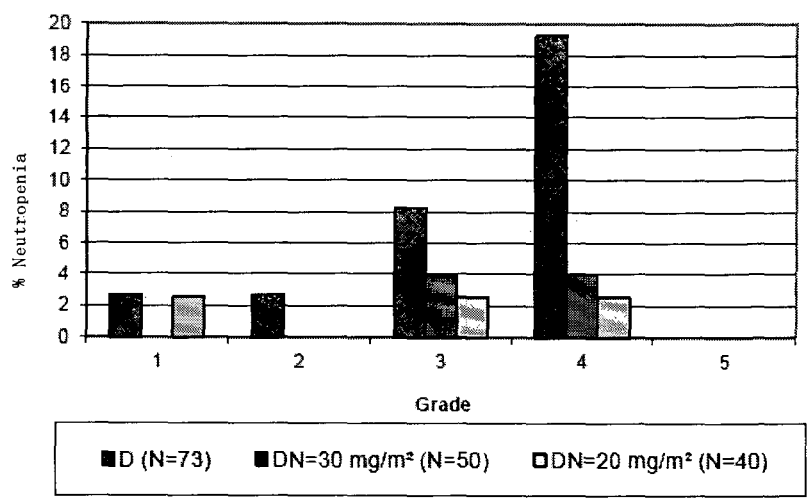

FIG. 5 shows that side effect such as neutropenia at different grades of severity was reduced by adding plinabulin to docetaxel treatment of NSCLC patient. Both 20 mg/m$^2$ or 30 mg/m$^2$ plinabulin added to docetaxel decreased neutropenia rate of docetaxel (D: Docetaxel; DN: Plinabulin and Docetaxel)

Figure 6:
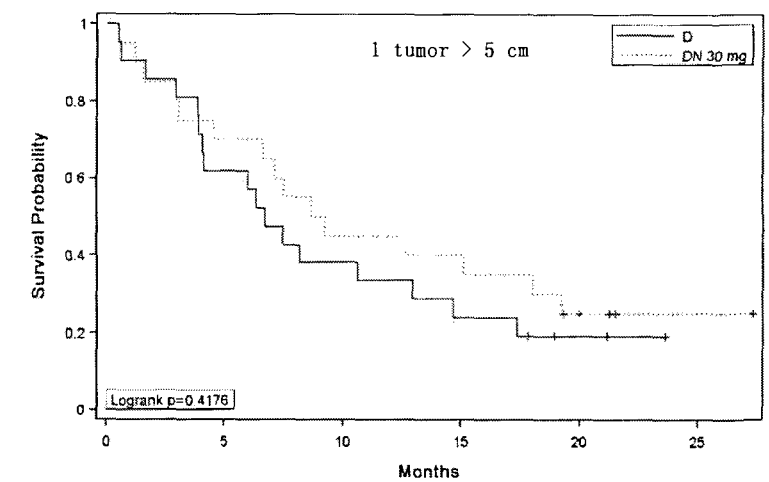
Figure 6:
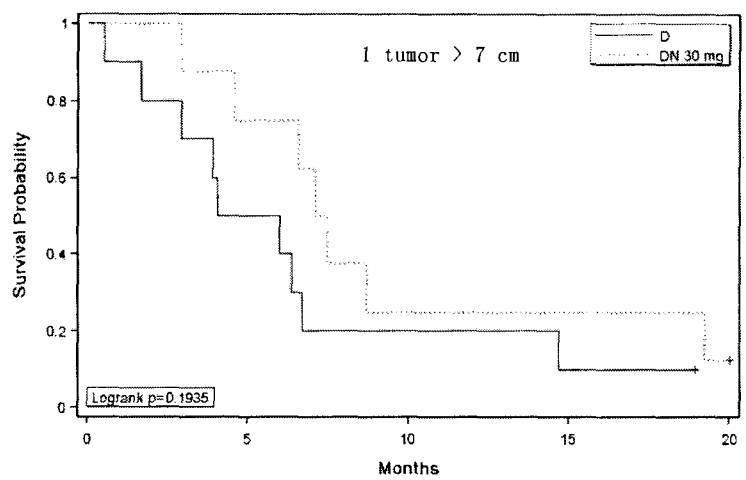

FIG. 6 shows overall survival Kaplan-Meier Curve in NSCLC patients (stage IIIb/IV, at least 1 prior chemotherapy). Arm DN: 30 mg/m$^2$ Plinabulin and 75 mg/m$^2$ docetaxel; Arm D: 75 mg/m$^2$ docetaxel. OS benefit increases in the Arm DN vs. Arm D as tumor size increases.

DETAILED DESCRIPTION

Through comprehensive and intensive research and screening, the inventor has unexpectedly developed a novel method for treatment of cancer by using plinabulin and docetaxel in combination. The experiments have shown optimum efficacy benefit using NSCLC MV522 animal model. The inventor has also discovered a series of combination method of using plinabulin and docetaxel to achieve optimum efficacy and safety benefit using NSCLC MV522 animal model experiments. On this basis, the present invention is completed.

In one embodiment according to the present invention, the optimum combination method can dramatically decrease side effects of taxane (such as docetaxel) in both NSCLC MV522 animal model, and NSCLC patients, and decrease G-CSF use in NSCLC patients, which are unexpected findings. No other VDA compound has been discovered with this effect in combination with docetaxel in cancer patient treatment.

In another embodiment according to the present invention, the optimum combination method achieved the most efficacy benefit in OS extension in a uniquely defined large tumor NSCLC patients, and in large tumor NSCLC MV522 animal model, which are novel and unexpected findings. No other VDA or anti-angiogenesis agent has been discovered in better efficacy in this unique defined large tumor NSCLC patient population.

Taxane Compound or the Derivatives Thereof

In the combination of the present invention, one important active ingredient is taxane compound or the derivatives thereof.

In the present invention, term "taxane compound" or "taxane" means a member of taxane family that has anti-cancer activity similar to paclitaxel based on the same or similar mechanism of paclitaxel. The exemplary taxane compounds include but are not limited to paclitaxel, docetaxel, and abraxane and so on. In the present invention, this term also include the derivatives and pharmaceutically acceptable salts thereof.

In the present invention, the amount of taxane compound is preferably administrated in routine manner and in routine dosage. For example, paclitaxel is usually administrated by 50-250 or 100-175 mg/m$^2$ via intravenous injection.

Plinabulin

In the combination of the present invention, another important active ingredient is plinabulin.

Figure 1:
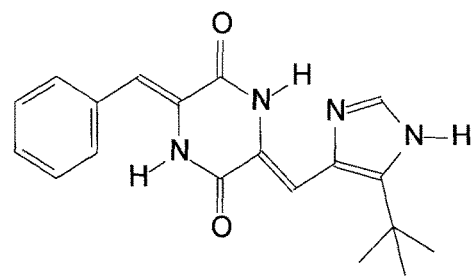
FIG. 1 shows chemical structure of Plinabulin.
Figure 2:
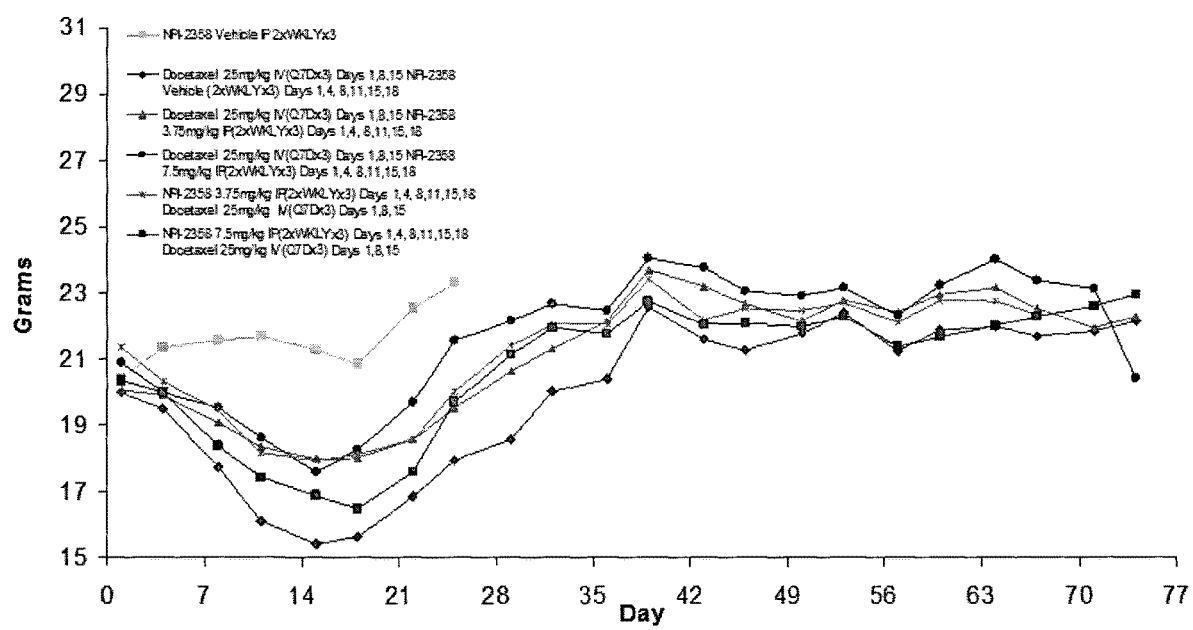
FIG. 2 shows mean percent weight change in Example 1 (NSCLC MV522 tumor model). Plinabulin (NPI-2358) addition to docetaxel reduced the docetaxel associated animal weight loss independent of each drug usage sequence (2 hour separation).

As used herein, terms "plinabulin", "NPI-2358" and "t-butyl dehydrophenylahistin" are exchangeable, and each means a synthetic, low molecular weight chemical entity, with chemical name of 2,5-piperazinedione, 3-[[5-(1,1dimethylethyl)-1H-imidazol-4-yl]methylene]-6-(phenylmethylene)-, (3Z,6Z)] as shown in FIG. 1. In the present invention, the above terms also include the pharmaceutically acceptable salts thereof.

NPI-2358 is discovered as an anti-cancer agent. WO 2004/054498 has disclosed the structure, synthesis and use of NPI-2358.

Plinabulin inhibits the dimerization of tubulin monomers. Its mechanism is in its effect on tumor vascularture, and thus cutting the blood supply for tumor growth, classified as vascular disrupting agent (VDA).

In the present invention, the amount of plinabulin is preferably administrated in routine manner and in routine dosage. Typically, plinabulin is administrated by 10-50 or 20-30 mg/m$^2$ via intravenous injection Combination, Pharmaceutical Composition and Kit In the present invention, a combination is provided, comprising an active ingredient (a) of a taxane compound; and an active ingredient (b) of plinabulin.

Further, a pharmaceutical composition is provided, comprising an active ingredient (a) of a taxane compound; an active ingredient (b) of plinabulin; and (c) a pharmaceutically acceptable carrier.

The dosage forms and preparation methods for the pharmaceutical composition of the present invention are not particularly limited, and the composition can be made into various dosage forms such as tablets, capsules, granules, sustained-release agents, injections, and the like by conventional processes in the art. A preferred dosage form is the oral dosage form.

In the invention, a kit is also provided, comprising:

(i) a first container containing a first medicament which comprises a taxane compound as an active ingredient (a) and an optional pharmaceutically acceptable carrier; and (ii) a second container containing a second medicament which comprises plinabulin as an active ingredient (b) and a optional pharmaceutically acceptable carrier;

(iii) an instruction recording an administration of the active ingredient (a) in combination with the active ingredient (b) for treating and/or preventing cancer.

The combination, formulations and kits of the present invention are useful for preventing and/or treating cancer.

The combination of the invention may be administrated together or in sequence. Preferably, the active ingredient (a) of taxane is administered first, followed by administration of the active ingredient (b) of plinabulin within 0.5-72 hr, preferably within 0.5-24 hrs, more preferably within 1-24 hrs, thereby significantly improving the efficacy and the patient's compliance, and significantly reducing the side effect of taxane such as neutropenia.

Of course, the effective dosage of the active ingredients can be varied according to the administration mode and the severity of the disease to be treated.

Treatment with Combination of Plinubulin and Taxane

The present invention provides an optimum method to use plinabulin and docetaxel to treat cancer subjects.

In the invention, a method for treating and preventing cancer by using two active ingredients is provided, which comprises administrating to a mammal subject (such as human) an effective amount of an active ingredient (a) of a taxane compound and an active ingredient (b) of plinabulin, or administrating a first medicament comprising the active ingredient (a) and a second medicament the active ingredient (b).

The two active ingredients or pharmaceutical compositions of the present invention may be administrated by conventional routes, including (but not limited to): intramuscular, intraperitoneal, intravenous, subcutaneous, intradermal, oral, or topical administration. Preferred routes of administration include oral administration.

The medicaments of the invention can be solid compositions for convenient administration, especially the tablets and solid filled or liquid-filled capsules. Preferably, the medicament or pharmaceutical composition is formulated as liquid formulation, or a lyophilized formulation or other suitable injection form.

Furthermore, the two active ingredients or drugs of the present invention can be used in combination with other drugs for treating cancer (such as cis-platin, paclitaxel, anti-tumor antibodies).

In the examples of the present invention, the inventor evaluated the antitumor activity of plinabulin in the MV522 lung cancer xenograft model. The in vivo efficacy of plinabulin was determined alone and in combination with docetaxel. Tumor growth inhibition (TGI) of plinabulin (3.75 and 7.5 mg/kg), docetaxel (15 and 25 mg/kg), and the combination was determined in the MV522 tumor model. Scheduling of the drug combinations was also conducted by administering one of the agents 2 hours after the first drug was given. Significant endpoints for this experiment included mean tumor growth inhibition (TGI) or regression, animal weight loss, potential toxicity, and tumor growth delay (TGD). The primary endpoint for the TGI study was the day that the mean NPI-2358 Vehicle tumor volume reached 1.2 cm$^3$. The endpoint for the TGD study was when each tumor reached a volume of 1.5 cm$^3$. In addition, an amendment was conducted to compare the efficacy of docetaxel and the combination of NPI-2358+docetaxel in large tumors (1.5 cm$^3$).

Animals were implanted with cancer cells harvested from tissue culture and allowed to establish tumors in nude mice. Treatment initiated when the average tumor volume of approximately 105 mm$^3$ was reached. No significant animal weight loss occurred in any of plinabulin single agent groups demonstrating that the drug was well tolerated at the given doses and schedule. As expected, significant animal weight loss was observed following treatment with docetaxel. Unexpectedly, the addition of NPI-2358 to docetaxel in the combination groups reduced the docetaxel associated weight loss (Table 2).

Treatment with plinabulin as a single agent induced a slight decrease in tumor volume compared to vehicle control, while docetaxel treatment resulted in a strong decrease in tumor burden. Importantly, the addition of plinabulin enhanced the antitumor activity of docetaxel in this model.

This effect was most prominent in the groups receiving docetaxel first followed by plinabulin, such as 2 hours later (Table 3). Furthermore, this drug combination was more effective than single agent docetaxel at reducing tumor burden in large tumors (1.5 cm$^3$) (Table 4).

To further explore the plinabulin and docetaxel combination schedule of administration, the inventor investigated the in vivo efficacy of plinabulin administered 1, 4, and 24 hours after docetaxel treatment in MV522 human lung cancer xenograph model in mice. Experimental design was similar to the animal study discussed above. The additional of plinabulin to docetaxel in the combination groups reduced the docetaxel associated animal weight loss. The weight loss trend was similar among the different groups whether plinabulin was given 1, 4, or 24 hours following docetaxel treatment (Table 6). In addition, the addition of plinabulin enhanced the antitumor activity of docetaxel.

There was not a dramatic difference in tumor burden whether plinabulin was given 1, 4 or 24 hours following docetaxel treatment (Table 7). The 1 hour plinabulin after 15 mg/kg docetaxel groups produced slightly smaller tumors than the 4 and 24-hour groups (Table 7).

Following this initial study, animals with similar tumor burden were re-treated to evaluate the effects of the plinabulin and docetaxel combination on large tumors. The plinabulin and docetaxel combination produced a more pronounced decrease in tumor burden compared to docetaxel treatment alone. Unexpectedly, the inventor discovered that plinabulin and docetaxel combination is effective against large established tumors (Table 8).

The investor applied the optimum plinabulin and docetaxel combination treatment schedule derived from MV522 animal studies in NSCLC patients. Patients received therapy on Day 1 and Day 8 in 3-week cycles. Therapy on Day 1 consisted of 75 mg/m$^2$ docetaxel administered via intravenous infusion (IV) over 1 hour, followed 2 hours later (from the time the docetaxel infusion begins) by 30 mg/m$^2$ plinabulin administered via intravenous infusion (IV) over 30 minutes. Therapy on Day 8 consisted of 20 mg/m² or 30 mg/m² plinabulin administered via intravenous infusion (IV) over 30 minutes.

The tolerability profile for plinabulin when added to docetaxel is better than docetaxel alone. Due to unbearable docetaxel side effects, the initial dose of 75 mg/m² docetaxel was decreased in 10% of patients (5 of 50) in the plinabulin 30 mg/m² plus docetaxel treatment arm whereas, the percent in the matched docetaxel alone arm was much higher at 18.2% of patients (10 of 55).

Of particular interest, patients in the plinabulin 30 mg/m² plus docetaxel arm had a statistically significantly lower rate of neutropenia (for all events and those events ≥Grade 3) than patients in the matched docetaxel alone arm.

Neutropenia is the docetaxel side effect that is most severe. Neutropenia was seen in 36.4% of patients in this same docetaxel alone arm, consistent with historical data. In contrast, the incidence of neutropenia in the plinabulin 30 mg/m² plus docetaxel treated arm at 8% was significantly lower than the matched docetaxel alone arm ($p<0.01$).

Similar results to the above were observed in the plinabulin 20 mg/m² plus docetaxel study arm and its matched docetaxel treatment arm. Less G-CSF was used in the combination group compared with the docetaxel group.

The novel finding that plinabulin can decrease docetaxel's neutropenia rate is unexpected.

The inventor also performed extensive analyses and unexpectedly identified a subgroup which reacts to the plinabulin and docetaxel combination. Of the subgroup analyses, the one defined as "at least one tumor with a diameter size greater than 3 cm" was the subgroup in which plinabulin 30 mg/m² plus docetaxel (OS=11.5 M) had the largest significant OS benefit when compared with the matched docetaxel treated group (OS=7.8 M) (FIG. 6). The OS benefit in the combination group compared with the docetaxel group persists in other larger tumor groups (1 tumor >5 cm, or >7 cm, FIG. 6). The investor has discovered a uniquely defined large tumor group which benefit from the optimum plinabulin and docetaxel combination, which was never reported before in any literature. None of approved tumor vasculature targeting agent has been reported to show any favor in large tumor NSCLC populations.

In summary, this is the first invention that has discovered the optimum combination scheme for plinabulin and docetaxel to achieve enhanced efficacy in uniquely defined large tumor patient population and dramatically decrease neutropenia rate of docetaxel in all patients. The invention provides new use of Plinabulin in combination with other chemotherapy agents to treat large tumor in multiple cancer indications. The invention further provides new use of Plinabulin combined with other taxane compounds to decrease taxane compounds' debilitating neutropenia side effects.

The main advantages of the present invention include:

(a) It discloses the effect of taxane in combination with plinabulin in the prevention of cancer (such as lung cancer), and provides a method of treatment by using the optimum combination of taxane and plinabulin.

(b) Taxane and plinabulin combination are relatively safe.

(c) The sequentially administration of taxane and plinabulin possesses synergistic inhibition of tumors, and has medically relevant statistical significance, thereby tolerance to taxane is increased and the side effects are reduced.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1

In vivo evaluation of plinabulin (NPI-2358) as a single agent and in combination with docetaxel in the MV522 human non-small cell lung tumor xenograph model in athymic nu/nu mice The objective of the example was to determine potential additive or synergistic effects of plinabulin in combination with docetaxel in the MV522 model by exploring the scheduling of the drug combination explored by administering one of the agents 2 hours after the first drug was given. Significant endpoints for this experiment included mean tumor growth inhibition (TGI) or regression, tumor growth delay (TGD) in large tumor, weight loss, and mortality.

Experimental Design:

Materials and Methods

Model Information—

Female nude mice (Hsd: Athymic Nude-Foxn1$^{nu}$) between 5 and 6 weeks of age weighing approximately 20 grams were obtained from Harlan, Inc. (Madison, Wis.). MV522 is a conventional human NSC metastatic lung tumor cell line (U.S. Pat. No. 7,700,615 or 7,629,380). Animals were injected subcutaneously (SC) with approximately $1 \times 10^7$ MV522 cells harvested from tissue culture. When tumors grew to approximately 105 cubic millimeters (mm³) in size (3 days following implantation), animals were pair-matched by tumor size into treatment and control groups; each treatment group contained eight mice. Animals were ear-tagged and followed individually throughout the experiment.

Study Design and Dosing—

Initial doses were administered on Day 1 following pair-matching. The experiment was carried out as a tumor growth inhibition (TGI) and tumor growth delay (TGD) study. Group 1 endpoint was when tumor volume reached 1.2 cm³ (TGI) and the treated groups endpoint was when each individual animal's tumor volume reached 1.5 cm³ (TGD). NPI-2358 in vehicle (8% Solutol® HS15, 12% PG, 80% D5W) was administered by intraperitoneal (IP) injection on a thrice weekly for two weeks −1 day schedule (3×WKLY× 2−1) or a twice weekly for three weeks schedule (2×WKLY× 3) at the doses listed below (Table 1). To serve as negative controls, NPI-2358 vehicle and docetaxel vehicle were injected IP on a 2×WKLY×3 schedule and IV on a Q2D×3 schedule, respectively. Docetaxel was administered by intravenous (IV) injection via tail vein at 15 mg/kg once every other day for three treatments (Q2D×3) or at 25 mg/kg on a Q7D×3 schedule (every 7 day for three treatment). Docetaxel and docetaxel vehicle were administered two hours prior to NPI-2358 vehicle and NPI-2358, respectively, in Groups 7-9 and 12-14. For Groups 10, 11, 15, and 16, NPI-2358 was given two hours prior to docetaxel.

TABLE 1

Study Design

| Group | Compound | Schedule | Dose (mg/kg) | Dosing Days | Route |
|---|---|---|---|---|---|
| 1 | Untreated Control | — | — | — | — |
| 2 | Docetaxel Vehicle | Q2Dx3 | — | 1, 3, 5 | IV |

TABLE 1-continued

Study Design

| Group | Compound | Schedule | Dose (mg/kg) | Dosing Days | Route |
|---|---|---|---|---|---|
| 3 | NPI-2358 Vehicle | 2xWKLYx3 | — | 1, 4, 8, 11, 15, 18 | IP |
| 4 | NPI-2358 | 3xWKLYx2-1 | 7.5 | 1, 3, 5, 8, 11 | IP |
| 5 | NPI-2358 | 2xWKLYx3 | 3.75 | 1, 4, 8, 11, 15, 18 | IP |
| 6 | NPI-2358 | 2xWKLYx3 | 7.5 | 1, 4, 8, 11, 15, 18 | IP |
| 7 | Docetaxel | Q2Dx3 | 15 | 1, 3, 5 | IV |
|   | NPI-2358 Vehicle | 3xWKLYx2-1 | — | 1, 3, 5, 8, 11 | IP |
| 8 | Docetaxel | Q2Dx3 | 15 | 1, 3, 5 | IV |
|   | NPI-2358 | 3xWKLYx2-1 | 3.75 | 1, 3, 5, 8, 11 | IP |
| 9 | Docetaxel | Q2Dx3 | 15 | 1, 3, 5 | IV |
|   | NPI-2358 | 3xWKLYx2-1 | 7.5 | 1, 3, 5, 8, 11 | IP |
| 10 | NPI-2358 | 3xWKLYx2-1 | 3.75 | 1, 3, 5, 8, 11 | IP |
|   | Docetaxel | Q2Dx3 | 15 | 1, 3, 5 | IV |
| 11 | NPI-2358 | 3xWKLYx2-1 | 7.5 | 1, 3, 5, 8, 11 | IP |
|   | Docetaxel | Q2Dx3 | 15 | 1, 3, 5 | IV |
| 12 | Docetaxel | Q7Dx3 | 25 | 1, 8, 15 | IV |
|   | NPI-2358 Vehicle | 2xWKLYx3 | — | 1, 4, 8, 11, 15, 18 | IP |
| 13 | Docetaxel | Q7Dx3 | 25 | 1, 8, 15 | IV |
|   | NPI-2358 | 2xWKLYx3 | 3.75 | 1, 4, 8, 11, 15, 18 | IP |
| 14 | Docetaxel | Q7Dx3 | 25 | 1, 8, 15 | IV |
|   | NPI-2358 | 2xWKLYx3 | 7.5 | 1, 4, 8, 11, 15, 18 | IP |
| 15 | NPI-2358 | 2xWKLYx3 | 3.75 | 1, 4, 8, 11, 15, 18 | IP |
|   | Docetaxel | Q7Dx3 | 25 | 1, 8, 15 | IV |
| 16 | NPI-2358 | 2xWKLYx3 | 7.5 | 1, 4, 8, 11, 15, 18 | IP |
|   | Docetaxel | Q7Dx3 | 25 | 1, 8, 15 | IV |

In combination groups 7-9 and 12-14, docetaxel was given 2 hours prior to NPI-2358 or NPI-2358 vehicle.
In combination groups 10, 11, 15, and 16, NPI-2358 was given 2 hours prior to docetaxel.

Data Collection and Statistical Analysis

Animal Weights—

Individual and group mean weights ±SD and percent weight change were recorded twice weekly until study completion beginning Day 1. Group weights on Day 42 and weight nadir values are reported.

Moribundity/Mortality—

Animals were observed twice weekly for general moribundity and daily for mortality.

Tumor Volume—

Individual and group mean tumor volumes ±SEM were recorded twice weekly (24 hours after dosing until study completion (mean control tumor volume=1.2 cm$^3$, Day 25) beginning Day 1. Tumor measurements were converted to cubic millimeter tumor volume using the formula below:

Tumor Volume (mm$^3$)=Width$^2$ (mm)×Length (mm)× 0.52

Tumor Necrosis—

Degree of tumor necrosis was rated at each tumor measurement using the following arbitrary index:

| N0 | None | No Visible Necrosis |
|---|---|---|
| N1 | Slight | Reddened or Inflamed; Intact Tumor |
| N2 | Mild | <10% Tumor Necrosis |
| N3 | Moderate | ≥10 and ≤50% Tumor Necrosis |
| N4 | Severe | >50% Tumor Necrosis |

Notable differences in tumor necrosis between treated and control groups were reported.

Tumor Growth Inhibition—

The TGI portion of the study was completed on Day 25 once the designated control group (Group 3, NPI-2358 vehicle) reached a mean tumor volume of approximately 1.2 cm$^3$ which is separate from the TGD study. Mice were weighed and caliper tumor measurements taken. Tumor growth inhibition (TGI) values were calculated for each group containing treated animals using the formula below:

$$1 - \frac{\text{Mean Final Tumor Volume (Treated)} - \text{Mean Initial Tumor Volume (Treated)}}{\text{Mean Final Tumor Volume (Control)} - \text{Mean Initial Tumor Volume (Control)}} \times 100\%$$

Animals experiencing complete tumor responses or animals experiencing technical or drug-related deaths were censored from final TGI calculations; however animals experiencing partial tumor responses were included in the final TGI calculations. The National Cancer Institute (NCI) criteria for compound activity is TGI>58%. TGI values for each treatment group are reported at study completion; these calculations are based on the final study day.

Tumor Growth Delay—

This arm of the study was ended on Day 74 at the sponsor's request. At TGI study completion (Day 25), individual tumor volumes from control and treatment groups were reviewed and those greater than or equal to the designated TGD tumor volume endpoint (1.5 cm$^3$) were removed from the study and each animal assigned a day of sacrifice value based on the day it reached the endpoint. Upon TGD study completion, a Median Day of Sacrifice (MDS) was calculated for the control (C) and each treatment (T) group and used to determine tumor growth delay (T-C) using the following equations:

MDS=Median [Σ$_{IDS}$] T-C=MDS$_{Treated}$-MDS$_{Control}$

Where IDS (Individual Day of Sacrifice) is the day when each animal reached its tumor volume endpoint (1.5 cm$^3$); only animals reaching this endpoint were included in TGD calculations. Gross or net log$_{10}$ cell kill for each treatment group was determined using the following equations:

$$\text{Gross Log}_{10} \text{ Cell Kill} = \frac{(T-C)}{(3.32)(Td)}$$

Where (T)=median day of death for the treated group, (C)=median day of death for the control group (NPI-2358 vehicle group), and (Td) is the tumor-volume doubling time estimated from a log-linear plot of log phase tumor growth (100-800 mm$^3$) over time in the control group; (3.32) is the number of doublings required for a population to increase one log$_{10}$ unit. Weight and tumor data from individual animals experiencing technical or drug-related deaths was censored from final group calculations and statistical analyses. Long-term survivors (animals not reaching the tumor volume endpoint by the preset time period (LTS)) are not included in these calculations. For comparison of activity with standard agent(s), gross or net log$_{10}$ cell-kill values were converted to an arbitrary activity rating below:

| Antitumor Activity | Gross Log$_{10}$ Cell-Kill |
|---|---|
| Highly Active +++++ | =5.0 |
| ++++ | 4.0-4.9 |
| +++ | 3.0-3.9 |
| ++ | 2.0-2.9 |
| + | 1.0-1.9 |
| Inactive | <1.0 |

Net log$_{10}$ cell-kill is utilized for test agents administered for less than five days of total treatments while activity of agents dosed for five or more treatment days are calculated using gross log cell-kill; an active rating of (+++) to (++++) is needed to effect partial or complete responses.

Partial/Complete Tumor Response—

Individual mice possessing tumors measuring less than on Day 1 were classified as having partial response (PR) and a percent tumor regression (% TR) value is determined using the formula below:

$$1 - \frac{\text{Final Tumor Volume (mm}^3)}{\text{Initial Tumor Volume (mm}^3)} \times 100\%$$

If partial tumor responses are reported in multiple animals within one group, a mean PR value was determined. Individual mice lacking palpable tumors were classified as undergoing complete response (CR). The number of partial and complete responses and percent tumor regression is reported for each treatment group at study completion; these calculations are based on the final study day.

TGI Statistics—

Statistical analyses were carried out between treated and control groups comparing final tumor volume. For two or more treatment groups, a two-tailed One-Way Analysis of Variance (ANOVA) followed by the Dunnett's multiple comparisons test was employed. An unpaired, two-tailed student t-test was used to compare one treated group to control. Weight and tumor data from individual animals experiencing technical or drug-related deaths were censored from analysis. However, weight and tumor data from animals reporting partial or complete responses were included in these calculations.

TGD Statistics—

A Log-rank test was used to determine statistically significant differences in overall survival experience between each treated group compared to control and as utilized is equivalent to the Mantel-Haenszel test. If a drug is evaluated at multiple concentrations on the same route and schedule, a Log-rank test from trend is also performed. Weight and tumor data from individual animals experiencing technical or drug-related deaths was censored from analysis. However, weight and tumor data from animals reporting partial or complete regressions or long term survivors were included in these calculations. All analyses were performed using GraphPad Prism® software (version 5.0).

Results

No significant animal weight loss occurred in any of plinabulin single agent groups demonstrating that the drug was well tolerated at the given doses and schedule. As expected, significant animal weight loss was observed following treatment with docetaxel.

Unexpectedly, the addition of NPI-2358 to docetaxel in the combination groups reduced the docetaxel associated weight loss (Table 2).

TABLE 2

Animal Weight and Drug Toxicity Results: Control, Single Agent, and Combination Groups

| GROUP | DOSE | ROUTE/SCHEDULE | FINAL WEIGHT DATA (DAY 25) | | WEIGHT NADIR | |
|---|---|---|---|---|---|---|
| | | | MEAN (G) ± SD | % CHANGE | % CHANG | DAY |
| 1 Untreated Control | — | — | 24 ± 2 | +8 | 0 | 1 |
| 2 Docetaxel Vehicle | — | IV/Q2Dx3 | 22 ± 2 | +6 | −6 | 18 |
| 3 NPI-2358 Vehicle | — | IP/2xWKLYx3* | 23 ± 2 | +14 | 0 | 1 |
| 4 NPI-2358 | 7.5 | IP/3xWKLYx2-1§ | 24 ± 2 | +11 | −1 | 8 |
| 5 NPI-2358 | 3.75 | IP/2xWKLYx3* | 23 ± 1 | +15 | 0 | 1 |
| 6 NPI-2358 | 7.5 | IP/2xWKLYx3* | 25 ± 2 | +14 | 0 | 1 |
| 7 Docetaxel | 15 | IV/Q2Dx3 | 24 ± 2 | +17 | −23 | 11 |
| NPI-2358 Vehicle | — | IP/3xWKLYx2-1§ | | | | |
| 8 Docetaxel | 15 | IV/Q2Dx3 | 23 ± 2 | +19 | −22 | 11 |
| NPI-2358 | 3.75 | IP/3xWKLYx2-1 | | | | |
| 9 Docetaxel | 15 | IV/Q2Dx3 | 24 ± 2 | +15 | −15 | 11 |
| NPI-2358 | 7.5 | IP/3xWKLYx2-1§ | | | | |
| 10 NPI-2358 | 3.75 | IP/3xWKLYx2-1§ | 23 ± 2 | +17 | −17 | 11 |
| Docetaxel | 15 | IV/Q2Dx3 | | | | |
| 11 NPI-2358 | 7.5 | IP/3xWKLYx2-1§ | 24 ± 1 | +20 | −15 | 11 |
| Docetaxel | 15 | IV/Q2Dx3 | | | | |
| 12 Docetaxel | 25 | IV/Q7Dx3 | 18 ± 2 | −10 | −23 | 15 |
| NPI-2358 Vehicle | — | IP/2xWKLYx3* | | | | |
| 13 Docetaxel | 25 | IV/Q7Dx3 | 20 ± 3 | −3 | −11 | 15 |
| NPI-2358 | 3.75 | IP/2xWKLYx3* | | | | |
| 14 Docetaxel | 25 | IV/Q7Dx3 | 22 ± 3 | +3 | −16 | 15 |
| NPI-2358 | 7.5 | IP/2xWKLYx3* | | | | |
| 15 NPI-2358 | 3.75 | IP/2xWKLYx3* | 20 ± 3 | −4 | −14 | 15 |
| Docetaxel | 25 | IV/Q7Dx3 | | | | |
| 16 NPI-2358 | 7.5 | IP/2xWKLYx3* | 20 ± 2 | −3 | −19 | 18 |
| Docetaxel | 25 | IV/Q7Dx3 | | | | |

N = 8/GRP ON DAY 1
*Days of Injection: 1, 4, 8, 11, 15, 18
§Days of Injection: 1, 3, 5, 8, 11
In combination groups 7-9 and 12-14, docetaxel was given 2 hours prior to NPI-2358 or vehicle.
In combination groups 10, 11, 15, and 16, NPI-2358 was given 2 hours prior to docetaxel.

Treatment with plinabulin as a single agent induced a slight decrease in tumor volume compared to Vehicle control, while docetaxel treatment resulted in a strong decrease in tumor burden. Importantly, the addition of NPI-2358 enhanced the antitumor activity of docetaxel in this model. This effect was most prominent in the groups receiving docetaxel first followed by NPI-2358 2 hours later (Table 3). Furthermore, this drug combination was more effective than single agent docetaxel at reducing tumor burden in large tumors (1.5 cm$^3$) (Table 4).

TABLE 3

Tumor Volume and TGI Results: Control, Single Agent, and Combination Groups

| | GROUP | DOSE | ROUTE/SCHEDULE | FINAL TUMOR VOLUME (DAY 25) MEAN (MM$^3$) ± SEM | % TGI | #PR/CR | % TR |
|---|---|---|---|---|---|---|---|
| 1 | Untreated Control | — | — | 963 ± 114 | — | — | — |
| 2 | Docetaxel Vehicle | — | IV/Q2Dx3 | 1411 ± 75 | — | 0/0 | — |
| 3 | NPI-2358 Vehicle | — | IP/2xWKLYx3* | 1371 ± 88 | — | 0/0 | — |
| 4 | NPI-2358 | 7.5 | IP/3xWKLYx2-1$^§$ | 1222 ± 114 | 12 | 0/0 | — |
| 5 | NPI-2358 | 3.75 | IP/2xWKLYx3* | 1347 ± 82 | 2 | 0/0 | — |
| 6 | NPI-2358 | 7.5 | IP/2xWKLYx3* | 1215 ± 110 | 12 | 0/0 | — |
| 7 | Docetaxel | 15 | IV/Q2Dx3 | 259 ± 45 | 88 | 0/0 | — |
| | NPI-2358 Vehicle | — | IP/3xWKLYx2-1$^§$ | | | | |
| 8 | Docetaxel | 15 | IV/Q2Dx3 | 93 ± 33 | 99$^†$ | 4/2 | 42 |
| | NPI-2358 | 3.75 | IP/3xWKLYx2-1 | | | | |
| 9 | Docetaxel | 15 | IV/Q2Dx3 | 160 ± 25 | 96$^†$ | 2/0 | 59 |
| | NPI-2358 | 7.5 | IP/3xWKLYx2-1$^§$ | | | | |
| 10 | NPI-2358 | 3.75 | IP/3xWKLYx2-1$^§$ | 260 ± 73 | 88$^†$ | 2/0 | 57 |
| | Docetaxel | 15 | IV/Q2Dx3 | | | | |
| 11 | NPI-2358 | 7.5 | IP/3xWKLYx2-1$^§$ | 233 ± 30 | 90 | 0/0 | — |
| | Docetaxel | 15 | IV/Q2Dx3 | | | | |
| 12 | Docetaxel | 25 | IV/Q7Dx3 | 43 ± 4 | 107$^†$ | 8/0 | 58 |
| | NPI-2358 Vehicle | — | IP/2xWKLYx3* | | | | |
| 13 | Docetaxel | 25 | IV/Q7Dx3 | 36 ± 6 | 107$^†$ | 7/1 | 58 |
| | NPI-2358 | 3.75 | IP/2xWKLYx3* | | | | |
| 14 | Docetaxel | 25 | IV/Q7Dx3 | 27 ± 5 | 109$^†$ | 6/1 | 70 |
| | NPI-2358 | 7.5 | IP/2xWKLYx3* | | | | |
| 15 | NPI-2358 | 3.75 | IP/2xWKLYx3* | 48 12 | 104$^†$ | 6/0 | 67 |
| | Docetaxel | 25 | IV/Q7Dx3 | | | | |
| 16 | NPI-2358 | 7.5 | IP/2xWKLYx3* | 66 7 | 103$^†$ | 6/0 | 46 |
| | Docetaxel | 25 | IV/Q7Dx3 | | | | |

N = 8/GRP ON DAY 1
*Days of Injection: 1, 4, 8, 11, 15, 18
$^§$Days of Injection: 1, 3, 5, 8, 11
In combination Groups 7-9 and 12-14, docetaxel was given 2 hours prior to NPI-2358 or NPI-2358 vehicle.
In combination Groups 10, 11, 15, and 16, NPI-2358 was given 2 hours prior to docetaxel.
$^†$Value includes tumors with PR.

TABLE 4

MDS and TGD Results

| | GROUP | DOSE | ROUTE/SCHEDULE | MDS DAY ± SD | T-C | LOG$_{10}$ CELL KILL | ACTIVITY RATING | #LTS | #PR/C | % TR |
|---|---|---|---|---|---|---|---|---|---|---|
| 1 | Untreated Control | — | — | 34 ± 14 | — | — | — | 1 | 0/0 | — |
| 2 | Docetaxel Vehicle | — | IV/Q2Dx3 | 27 ± 3 | — | — | — | 0 | 0/0 | — |
| 3 | NPI-2358 Vehicle | — | IP/2xWKLYx3* | 29 ± 4 | — | — | — | 0 | 0/0 | — |
| 4 | NPI-2358 | 7.5 | IP/3xWKLYx2-1$^§$ | 31 ± 5 | 2 | 0.0 | — | 0 | 0/0 | — |
| 5 | NPI-2358 | 3.75 | IP/2xWKLYx3* | 29 ± 2 | 0 | 0.0 | — | 0 | 0/0 | — |
| 6 | NPI-2358 | 7.5 | IP/2xWKLYx3* | 29 ± 12 | 0 | 0.0 | — | 0 | 0/0 | — |
| 7 | Docetaxel | 15 | IV/Q2Dx3 | 45 ± 9 | 16 | 0.4 | — | 0 | 0/0 | — |
| | NPI-2358 Vehicle | — | IP/3xWKLYx2-1$^§$ | | | | | | | |
| 8 | Docetaxel | 15 | IV/Q2Dx3 | 53 ± 6 | 24 | 0.6 | — | 0 | 0/0 | — |
| | NPI-2358 | 3.75 | IP/3xWKLYx2-1 | | | | | | | |
| 9 | Docetaxel | 15 | IV/Q2Dx3 | 52 ± 10 | 23 | 0.6 | — | 0 | 0/0 | — |
| | NPI-2358 | 7.5 | IP/3xWKLYx2-1$^§$ | | | | | | | |
| 10 | NPI-2358 | 3.75 | IP/3xWKLYx2-1$^§$ | 53 ± 7 | 24 | 0.6 | — | 1 | 1/0 | 83 |
| | Docetaxel | 15 | IV/Q2Dx3 | | | | | | | |
| 11 | NPI-2358 | 7.5 | IP/3xWKLYx2-1$^§$ | 46 ± 2 | 17 | 0.4 | — | 0 | 0/0 | — |
| | Docetaxel | 15 | IV/Q2Dx3 | | | | | | | |
| 12 | Docetaxel | 25 | IV/Q7Dx3 | 68 ± 6 | 39 | 1.0 | + | 2 | 0/0 | — |
| | NPI-2358 Vehicle | — | IP/2xWKLYx3* | | | | | | | |
| 13 | Docetaxel | 25 | IV/Q7Dx3 | 67 ± 6 | 38 | 1.0 | + | 3 | 1/0 | 42 |
| | NPI-2358 | 3.75 | IP/2xWKLYx3* | | | | | | | |
| 14 | Docetaxel | 25 | IV/Q7Dx3 | 69 ± 8 | 40 | 1.1 | + | 1 | 0/0 | — |
| | NPI-2358 | 7.5 | IP/2xWKLYx3* | | | | | | | |
| 15 | NPI-2358 | 3.75 | IP/2xWKLYx3* | 67 ± 3 | 38 | 1.0 | + | 0 | 0/0 | — |
| | Docetaxel | 25 | IV/Q7Dx3 | | | | | | | |

TABLE 4-continued

MDS and TGD Results

| GROUP | DOSE | ROUTE/SCHEDULE | MDS DAY ± SD | T-C | LOG$_{10}$ CELL KILL | ACTIVITY RATING | #LTS | #PR/C | % TR |
|---|---|---|---|---|---|---|---|---|---|
| 16 NPI-2358 | 7.5 | IP/2xWKLYx3* | 61 ± 5 | 32 | 0.8 | + | 2 | 1/0 | 95 |
| Docetaxel | 25 | IV/Q7Dx3 | | | | | | | |

N = 8/GRP ON DAY 1
*Days of Injection: 1, 4, 8, 11, 15, 18
§Days of Injection: 1, 3, 5, 8, 11
In combination Groups 7-9 and 12-14, docetaxel was given 2 hours prior to NPI-2358 or NPI-2358 vehicle.
In combination Groups 10, 11, 15, and 16, NPI-2358 was given 2 hours prior to docetaxel.
*Days of Injection: 1, 4, 8, 11, 15, 18

Example 2

In vivo evaluation of plinabulin in combination with docetaxel in the MV522 human non-small cell lung tumor xenograph model in athymic nu/nu mice: schedule of drug administration The objective of the example was to evaluate the potential additive or synergistic effects of plinabulin (NPI-2358) in combination with docetaxel by administering NPI-2358 at various time points (1 h, 4 h, or 24 h) after docetaxel in the MV522 model. Significant endpoints for this experiment included mean tumor growth inhibition (TGI) or regression, tumor growth delay (TGD) in large tumor, weight loss, and mortality.

Experimental Design:
Materials and Methods
Model Information—

Female nude mice (Hsd: Athymic Nude-Foxn1$^{nu}$) between 5 and 6 weeks of age weighing approximately 20 grams were obtained from Harlan, Inc. (Madison, Wis.). Animals were injected subcutaneously (SC) with approximately 1×10$^7$ MV522 cells harvested from tissue culture (1:1 matrigel:media). When tumors grew to approximately 100 cubic millimeters (mm$^3$) in size, animals were pair-matched by tumor size into treatment and control groups. Animals were ear-tagged and followed individually throughout the experiment.

Original Study Design and Dosing—

Initial doses were administered on Day 1 following pair-matching. The experiment was carried out as both a tumor growth inhibition (TGI) and tumor growth delay (TGD) study. For TGI, the endpoint was when the average tumor volume of Group 1 reached 1.2 cm$^3$. For TGD, the endpoint was reached when each individual animal's tumor volume reached 1.0 cm$^3$. A 10 mg/ml stock vial of docetaxel was diluted in 0.9% saline on each day of dosing and administered intravenously (IV). The schedule and doses for each agent are listed in Table 5. Docetaxel vehicle (0.9% saline; IV; Days 1, 3, 5) plus NPI-2358 vehicle (8% Solutol® HS15, 12% PG, 80% D5W; IP; Days 1, 3, 5, 8, 11) was administered to serve as negative control.

TABLE 5

Study Design

| | #Animals | Compound | Hours after Docetaxel | Dose (mg/kg) | Route | Dosing Days |
|---|---|---|---|---|---|---|
| 1 | 8 | Docetaxel Vehicle | 0 | — | IV | 1, 3, 5 |
| | | NPI-2358 Vehicle | 1 | — | IP | 1, 3, 5, 8, 11 |
| 2 | 8 | Docetaxel | 0 | 15 | IV | 1, 3, 5 |
| | | NPI-2358 Vehicle | 1 | — | IP | 1, 3, 5, 8, 11 |
| 3 | 8 | Docetaxel | 0 | 15 | IV | 1, 3, 5 |
| | | NPI-2358 Vehicle | 4 | — | IP | 1, 3, 5, 8, 11 |
| 4 | 8 | Docetaxel | 0 | 15 | IV | 1, 3, 5 |
| | | NPI-2358 Vehicle | 24 | — | IP | 1, 3, 5, 8, 11 |
| 5 | 8 | Docetaxel | 0 | 15 | IV | 1, 3, 5 |
| | | NPI-2358 | 1 | 3.75 | IP | 1, 3, 5, 8, 11 |
| 6 | 8 | Docetaxel | 0 | 15 | IV | 1, 3, 5 |
| | | NPI-2358 | 4 | 3.75 | IP | 1, 3, 5, 8, 11 |
| 7 | 8 | Docetaxel | 0 | 15 | IV | 1, 3, 5 |
| | | NPI-2358 | 24 | 3.75 | IP | 1, 3, 5, 8, 11 |
| 8 | 8 | Docetaxel | 0 | 15 | IV | 1, 3, 5 |
| | | NPI-2358 | 1 | 7.5 | IP | 1, 3, 5, 8, 11 |
| 9 | 8 | Docetaxel | 0 | 15 | IV | 1, 3, 5 |
| | | NPI-2358 | 4 | 7.5 | IP | 1, 3, 5, 8, 11 |
| 10 | 8 | Docetaxel | 0 | 15 | IV | 1, 3, 5 |
| | | NPI-2358 | 24 | 7.5 | IP | 1, 3, 5, 8, 11 |
| 11 | 8 | Docetaxel | 0 | 25 | IV | 1, 8, 15 |
| | | NPI-2358 Vehicle | 1 | — | IP | 1, 4, 8, 11, 15, 18 |
| 12 | 8 | Docetaxel | 0 | 25 | IV | 1, 8, 15 |
| | | NPI-2358 Vehicle | 4 | — | IP | 1, 4, 8, 11, 15, 18 |
| 13 | 8 | Docetaxel | 0 | 25 | IV | 1, 8, 15 |
| | | NPI-2358 Vehicle | 24 | — | IP | 1, 4, 8, 11, 15, 18 |
| 14 | 8 | Docetaxel | 0 | 25 | IV | 1, 8, 15 |
| | | NPI-2358 | 1 | 3.75 | IP | 1, 4, 8, 11, 15, 18 |
| 15 | 8 | Docetaxel | 0 | 25 | IV | 1, 8, 15 |
| | | NPI-2358 | 4 | 3.75 | IP | 1, 4, 8, 11, 15, 18 |

TABLE 5-continued

Study Design

| | #Animals | Compound | Hours after Docetaxel | Dose (mg/kg) | Route | Dosing Days |
|---|---|---|---|---|---|---|
| 16 | 8 | Docetaxel | 0 | 25 | IV | 1, 8, 15 |
| | | NPI-2358 | 24 | 3.75 | IP | 1, 4, 8, 11, 15, 18 |
| 17 | 8 | Docetaxel | 0 | 25 | IV | 1, 8, 15 |
| | | NPI-2358 | 1 | 7.5 | IP | 1, 4, 8, 11, 15, 18 |
| 18 | 8 | Docetaxel | 0 | 25 | IV | 1, 8, 15 |
| | | NPI-2358 | 4 | 7.5 | IP | 1, 4, 8, 11, 15, 18 |
| 19 | 8 | Docetaxel | 0 | 25 | IV | 1, 8, 15 |
| | | NPI-2358 | 24 | 7.5 | IP | 1, 4, 8, 11, 15, 18 |

Data Collection and Statistical Analysis

The study in this example was completed on Day 24 once the designated control group reached a mean tumor volume of approximately 1.2 cm$^3$.

Animal Weights—

Individual and group mean weights ±SD and percent weight change were recorded twice weekly until study completion beginning Day 1. Group weights through Day 24 or 53 and weight nadir values are reported.

Moribundity/Mortality—
Same as in Example 1.
Tumor Volume—
Same as in Example 1.
Tumor Necrosis—
Same as in Example 1.
Partial/Complete Tumor Response—
Same as in Example 1.
Tumor Growth Inhibition—
Same as in Example 1.
TGI Statistics—
Same as in Example 1.
Tumor Growth Delay—

Same as in Example 1. This arm of the study was ended on Day 80 or 53 at the sponsor's request. Long-term survivors (animals not reaching the tumor volume endpoint by the preset time period (LTS)) were assigned an IDS value of the last study day (Day 80) and included in these calculations.

For comparison of activity with standard agent(s), gross or net log$_{10}$ cell-kill values were converted to an arbitrary activity rating below:

| Activity Rating | Treatment = <5 Days (Net Log$_{10}$ Cell-Kill) | Treatment = 5-20 Days (Gross Log$_{10}$ Cell-Kill) | Treatment >= 20 Days (Gross Log$_{10}$ Cell-Kill) |
|---|---|---|---|
| Highly Active | | | |
| ++++ | >2.6 | >2.8 | >3.4 |
| +++ | 1.6-2.6 | 2.0-2.8 | 2.5-3.4 |
| ++ | 0.9-1.5 | 1.3-1.9 | 1.7-2.4 |
| + | 0.5-0.8 | 0.7-1.2 | 1.0-1.6 |
| Inactive | | | |
| − | <0.5 | <0.7 | <1.0 |

Net log$_{10}$ cell-kill is utilized for test agents administered for less than five days of total treatments while activity of agents dosed for five or more treatment days are calculated using gross log cell-kill; an active rating of (+++) to (++++) is needed to effect partial or complete responses.

TGD Statistics—
Same as in Example 1.
Results

To further explore the plinabulin and docetaxel combination schedule of administration, the inventor investigated the in vivo efficacy of plinabulin administered 1, 4, and 24 hours after docetaxel treatment in MV522 human lung cancer xenograph model in mice. Experimental design was similar to the animal study discussed above. The additional of plinabulin to docetaxel in the combination groups reduced the docetaxel associated animal weight loss. The weight loss trend was similar among the different groups whether plinabulin was given 1, 4, or 24 hours following docetaxel treatment (Table 6).

TABLE 6

Animal Weight and Drug Toxicity Results - All Groups

| | Group | Hours after Docetaxel | Dose (mg/kg) | Final Weight - Day 24 AVG +/− SD (g) | % Change | NADIR % change | Day |
|---|---|---|---|---|---|---|---|
| 1 | Docetaxel Vehicle | 0 | — | 22 +/− 1 | +12 | 0 | 1 |
| | NPI-2358 Vehicle | 1 | — | | | | |
| 2 | Docetaxel | 0 | 15 | 22 +/− 1 | +13 | −14 | 10 |
| | NPI-2358 Vehicle | 1 | — | | | | |
| 3 | Docetaxel | 0 | 15 | 23 +/− 2 | +12 | −10 | 10 |
| | NPI-2358 Vehicle | 4 | — | | | | |
| 4 | Docetaxel | 0 | 15 | 23 +/− 2 | +17 | −10 | 10 |
| | NPI-2358 Vehicle | 24 | — | | | | |
| 5 | Docetaxel | 0 | 15 | 22 +/− 1 | +18 | −12 | 10 |
| | NPI-2358 | 1 | 3.75 | | | | |
| 6 | Docetaxel | 0 | 15 | 23 +/− 2 | +14 | −9 | 10 |
| | NPI-2358 | 4 | 3.75 | | | | |

TABLE 6-continued

Animal Weight and Drug Toxicity Results - All Groups

| | | | Final Weight - Day 24 | | NADIR | |
|---|---|---|---|---|---|---|
| Group | Hours after Docetaxel | Dose (mg/kg) | AVG +/− SD (g) | % Change | % change | Day |
| 7 Docetaxel | 0 | 15 | 23 +/− 2 | +15 | −12 | 10 |
| NPI-2358 | 24 | 3.75 | | | | |
| 8 Docetaxel | 0 | 15 | 22 +/− 1 | +15 | −10 | 10 |
| NPI-2358 | 1 | 7.5 | | | | |
| 9 Docetaxel | 0 | 15 | 23 +/− 1 | +19 | −13 | 10 |
| NPI-2358 | 4 | 7.5 | | | | |
| 10 Docetaxel | 0 | 15 | 22 +/− 1 | +17 | −11 | 10 |
| NPI-2358 | 24 | 7.5 | | | | |
| 11 Docetaxel | 0 | 25 | 18 +/− 2 | −10 | −13 | 17 |
| NPI-2358 Vehicle | 1 | — | | | | |
| 12 Docetaxel | 0 | 25 | 17 +/− 2 | −11 | −14 | 10 |
| NPI-2358 Vehicle | 4 | — | | | | |
| 13 Docetaxel | 0 | 25 | 17 +/− 3 | −12 | −20 | 17 |
| NPI-2358 Vehicle | 24 | — | | | | |
| 14 Docetaxel | 0 | 25 | 19 +/− 2 | −4 | −9 | 21 |
| NPI-2358 | 1 | 3.75 | | | | |
| 15 Docetaxel | 0 | 25 | 19 +/− 1 | −4 | −8 | 21 |
| NPI-2358 | 4 | 3.75 | | | | |
| 16 Docetaxel | 0 | 25 | 18 +/− 2 | −5 | −9 | 21 |
| NPI-2358 | 24 | 3.75 | | | | |
| 17 Docetaxel | 0 | 25 | 20 +/− 2 | −3 | −7 | 21 |
| NPI-2358 | 1 | 7.5 | | | | |
| 18 Docetaxel | 0 | 25 | 20 +/− 1 | +1 | −3 | 21 |
| NPI-2358 | 4 | 7.5 | | | | |
| 19 Docetaxel | 0 | 25 | 20 +/− 2 | −2 | −8 | 21 |
| NPI-2358 | 24 | 7.5 | | | | |

In addition, the addition of plinabulin appeared to enhance the antitumor activity of docetaxel. There was not a dramatic difference in tumor burden whether plinabulin was given 1, 4 or 24 hours following docetaxel treatment (Table 7). The 1 hour plinabulin after 15 mg/kg docetaxel groups produced slightly smaller tumors than the 4 and 24-hour groups (Table 7).

TABLE 7

Tumor Volume and TGI Results -All Groups

| Group | Hours after Docetaxel | Dose (mg/kg) | Final Tumor Volume (Day 24) Mean +/− SEM | % TGI | % TR (#) |
|---|---|---|---|---|---|
| 1 Docetaxel Vehicle | 0 | — | 1185 +/− 65 | — | — |
| NPI-2358 Vehicle | 1 | — | | | |
| 2 Docetaxel | 0 | 15 | 337 +/− 29 | 79 | — |
| NPI-2358 Vehicle | 1 | — | | | |
| 3 Docetaxel | 0 | 15 | 313 +/− 23 | 81 | — |
| NPI-2358 Vehicle | 4 | — | | | |
| 4 Docetaxel | 0 | 15 | 325 +/− 41 | 80 | — |
| NPI-2358 Vehicle | 24 | — | | | |
| 5 Docetaxel | 0 | 15 | 77 +/− 13 | 103 | 51 (5) |
| NPI-2358 | 1 | 3.75 | | | |
| 6 Docetaxel | 0 | 15 | 131 +/− 35 | 98 | 67 (3) |
| NPI-2358 | 4 | 3.75 | | | |
| 7 Docetaxel | 0 | 15 | 153 +/− 21 | 96 | 19 (1) |
| NPI-2358 | 24 | 3.75 | | | |
| 8 Docetaxel | 0 | 15 | 92 +/− 16 | 101 | 31 (3) |
| NPI-2358 | 1 | 7.5 | | | |
| 9 Docetaxel | 0 | 15 | 139 +/− 29 | 97 | 45 (3) |
| NPI-2358 | 4 | 7.5 | | | |
| 10 Docetaxel | 0 | 15 | 136 +/− 18 | 97 | 39 (2) |
| NPI-2358 | 24 | 7.5 | | | |
| 11 Docetaxel | 0 | 25 | 69 +/− 10 | 104 | 42 (7) |
| NPI-2358 Vehicle | 1 | — | | | |
| 12 Docetaxel | 0 | 25 | 65 +/− 9 | 104 | 45 (7) |
| NPI-2358 Vehicle | 4 | — | | | |
| 13 Docetaxel | 0 | 25 | 72 +/− 14 | 103 | 55 (7) |
| NPI-2358 Vehicle | 24 | — | | | |
| 14 Docetaxel | 0 | 25 | 37 +/− 6 | 106 | 64 (8) |
| NPI-2358 | 1 | 3.75 | | | |

TABLE 7-continued

Tumor Volume and TGI Results -All Groups

| Group | Hours after Docetaxel | Dose (mg/kg) | Final Tumor Volume (Day 24) Mean +/− SEM | % TGI | % TR (#) |
|---|---|---|---|---|---|
| 15 Docetaxel | 0 | 25 | 41 +/− 7 | 106 | 61 (8) |
| NPI-2358 | 4 | 3.75 | | | |
| 16 Docetaxel | 0 | 25 | 33 +/− 6 | 107 | 68 (8) |
| NPI-2358 | 24 | 3.75 | | | |
| 17 Docetaxel | 0 | 25 | 61 +/− 10 | 104 | 49 (7) |
| NPI-2358 | 1 | 7.5 | | | |
| 18 Docetaxel | 0 | 25 | 44 +/− 5 | 106 | 56 (8) |
| NPI-2358 | 4 | 7.5 | | | |
| 19 Docetaxel | 0 | 25 | 36 +/− 6 | 106 | 61 (7)/CR (1) |
| NPI-2358 | 24 | 7.5 | | | |

Following this initial study, animals with similar tumor burden were re-treated to evaluate the effects of the plinabulin and docetaxel combination on large tumors. The plinabulin and docetaxel combination produced a more pronounced decrease in tumor burden compared to docetaxel treatment alone. Unexpectedly, the inventor discovered that plinabulin and docetaxel combination is effective against large established tumors (Table 8).

TABLE 8

MDS and TGD Results - All Groups

| Group | Hours after Docetaxel | Dose (mg/kg) | MDS Day +/− SD | T-C | $LOG_{10}$ Cell Kill | Activity Rating |
|---|---|---|---|---|---|---|
| 1 Docetaxel Vehicle | 0 | — | 24 +/− 3 | — | — | — |
| NPI-2358 Vehicle | 1 | — | | | | |
| 2 Docetaxel | 0 | 15 | 38 +/− 3 | 14 | 0.6 | − |
| NPI-2358 Vehicle | 1 | — | | | | |
| 3 Docetaxel | 0 | 15 | 42 +/− 6 | 18 | 0.7 | + |
| NPI-2358 Vehicle | 4 | — | | | | |
| 4 Docetaxel | 0 | 15 | 40 +/− 7 | 16 | 0.6 | − |
| NPI-2358 Vehicle | 24 | — | | | | |
| 5 Docetaxel | 0 | 15 | 52 +/− 4 | 28 | 1.1 | + |
| NPI-2358 | 1 | 3.75 | | | | |
| 6 Docetaxel | 0 | 15 | 42 +/− 6 | 18 | 0.7 | + |
| NPI-2358 | 4 | 3.75 | | | | |
| 7 Docetaxel | 0 | 15 | 45 +/− 4 | 21 | 0.9 | + |
| NPI-2358 | 24 | 3.75 | | | | |
| 8 Docetaxel | 0 | 15 | 52 +/− 11 | 28 | 1.1 | + |
| NPI-2358 | 1 | 7.5 | | | | |
| 9 Docetaxel | 0 | 15 | 49 +/− 7 | 25 | 1.0 | + |
| NPI-2358 | 4 | 7.5 | | | | |
| 10 Docetaxel | 0 | 15 | 47 +/− 6 | 23 | 0.9 | + |
| NPI-2358 | 24 | 7.5 | | | | |
| 11 Docetaxel | 0 | 25 | 63 +/− 10 | 39 | 1.6 | ++ |
| NPI-2358 Vehicle | 1 | — | | | | |
| 12 Docetaxel | 0 | 25 | 56 +/− 4 | 32 | 1.3 | ++ |
| NPI-2358 Vehicle | 4 | — | | | | |
| 13 Docetaxel | 0 | 25 | 59 +/− 10 | 35 | 1.4 | ++ |
| NPI-2358 Vehicle | 24 | — | | | | |
| 14 Docetaxel | 0 | 25 | 66 +/− 9 | 42 | 1.7 | ++ |
| NPI-2358 | 1 | 3.75 | | | | |
| 15 Docetaxel | 0 | 25 | 59 +/− 6 | 35 | 1.4 | ++ |
| NPI-2358 | 4 | 3.75 | | | | |
| 16 Docetaxel | 0 | 25 | 59 +/− 12 | 35 | 1.4 | ++ |
| NPI-2358 | 24 | 3.75 | | | | |
| 17 Docetaxel | 0 | 25 | 59 +/− 9 | 35 | 1.4 | ++ |
| NPI-2358 | 1 | 7.5 | | | | |
| 18 Docetaxel | 0 | 25 | 61 +/− 9 | 37 | 1.5 | ++ |
| NPI-2358 | 4 | 7.5 | | | | |
| 19 Docetaxel | 0 | 25 | 63 +/− 7 | 39 | 1.6 | ++ |
| NPI-2358 | 24 | 7.5 | | | | |

Example 3

Evaluation of the optimum plinabulin and docetaxel combination in treating advanced non-small cell lung cancer patients Objectives Primary:

To compare the overall survival of patients with NSCLC treated with docetaxel to patients treated with docetaxel+plinabulin.

Secondary:

1. To compare the response rate, duration of response, 6-month survival, and progression free survival in patients with NSCLC treated with docetaxel to patients with docetaxel+plinabulin;
2. To compare the safety and adverse events profile of docetaxel to docetaxel+plinabulin.

Study Design

This was an open-label study in patients with advanced NSCLC that had progressed after treatment with at least 1 chemotherapy regimen. Patients were randomized to receive either docetaxel plus plinabulin (DN) or docetaxel alone (75 mg/m$^2$) (D). 2 dosing cohorts were investigated:

1) 30 mg/m$^2$ dosing cohort: Approximately 110 patients were to be randomized (1:1) to receive either docetaxel plus plinabulin at 30 mg/m$^2$ (DN 30 mg/m$^2$ arm) or docetaxel alone (D arm);
2) 20 mg/m$^2$ dosing cohort: Approximately 57 patients were to be randomized (2:1) to receive either docetaxel plus plinabulin at 20 mg/m$^2$ (DN 20 mg/m$^2$ arm) or docetaxel (D arm) alone.

Dosing Regimen

Patients received therapy on Day 1 and Day 8 in 3-week cycles.

Therapy on Day 1 consisted of 75 mg/m$^2$ docetaxel administered via intravenous infusion (IV) over 1 hour, followed 2 hours later (from the time the docetaxel infusion began) by placebo (Arm D) or 30 mg/m$^2$ or 20 mg/m$^2$ plinabulin (Arm DN) DN administered via intravenous infusion (IV) over 30 minutes. Oral dexamethasone (16 mg) was given the day prior to, the day of and the day following docetaxel infusion (Day 1). Therapy on Day 8 consisted of placebo (Arm D) or 30 mg/m$^2$ or 20 mg/m$^2$ plinabulin (Arm DN) administered via intravenous infusion (IV) over 30 minutes.

In patients experiencing drug related Grade >2 treatment emergent adverse events (except alopecia, anorexia, and fatigue) according to the CTCAE (v3.0) treatment may be delayed until the adverse event has recovered to <Grade 1. Safety laboratory tests must meet the following criteria prior to treatment with docetaxel at the beginning of each subsequent cycle: AST<2.5×ULN, ALT≤2.5×ULN (<1.5×ULN if alkaline phosphatase is >=2.5×ULN); bilirubin <=ULN; hemoglobin >=9 g/dL, absolute neutrophil count >=1.5× 10$^9$/L and platelets>=100×10$^9$/L. Dose reductions may be implemented for patients who experience recurrent or specific severe toxicities.

Target Population

Patients with stage IIIb/IV non-small cell lung cancer that has progressed after treatment with at least one chemotherapy regimen.

Inclusion Criteria

1. Male and females >=18 years of age.
2. ECOG performance status <1.
3. Pathologically or histologically confirmed advanced non-small cell lung cancer (unresectable Stage IIIb or IV) that has progressed after treatment with at least one chemotherapy regimen. Measurable disease is not required for enrollment into this trial.
4. All Adverse Events of any prior chemotherapy, surgery, or radiotherapy, must have resolved to CTCAE (v. 3.0) Grade <2.
5. The following laboratory results, within 14 days:
Hemoglobin >9 g/dL
Absolute neutrophil count >=1.5×10$^9$/L
Platelet count >=100×10$^9$/L
Serum bilirubin <ULN
AST and ALT<2.5×ULN (<1.5×ULN if alkaline phosphatase is >=2.5×ULN).
6. Signed informed consent.

Exclusion Criteria

1. Administration of certain chemotherapy, biological, immunotherapy, radiation therapy or investigational agent (therapeutic or diagnostic) within 21 days prior to receipt of study medication. Major surgery, other than diagnostic surgery, within 6 weeks before first study drug administration.
2. Significant cardiac history:
   History of myocardial infarction or ischemic heart disease;
   History of clinically significant arrhythmias; uncontrolled arrhythmia or a requirement for anti-arrhythmics;
   History of congenital QT prolongation;
   Left bundle branch block;
   ECG findings consistent with ischemic heart disease;
   New York Heart Association Class III or IV cardiac disease
   Uncontrolled hypertension: blood pressure consistently greater than 150 mm Hg systolic and 100 mm Hg diastolic in spite of antihypertensive medication.
3. Prior treatment with tumor vascular disrupting agents.
4. Prior seizure disorder.
5. Brain metastases. Patients who demonstrate signs or symptoms of brain metastases should be imaged with CT or MRI. Patients who have brain metastases that have been previously treated and reimaged after treatment and whose lesions are stable without interim development of new lesions may be enrolled.
6. History of significant gastrointestinal disease such as ileus, bowel obstruction, hemorrhagic diarrhea, inflammatory bowel disease, active uncontrolled peptic ulcer disease. (Concomitant therapy with ranitidine or its equivalent and/or omeprazole or its equivalent is acceptable).
7. History of peri-operative pelvic radiation therapy, whole abdomen radiation therapy, or >=Grade 2 residual gastrointestinal symptoms from radiation therapy.
8. Active uncontrolled bacterial, viral, or fungal infection, requiring systemic therapy.
9. Known infection with human immunodeficiency virus (HIV), or active hepatitis A, B, or C.
10. Patients with a prior hypersensitivity reaction to any product containing polysorbate 80, taxanes, Solutol and/or propylene glycol.

11. Pregnant or breast-feeding women. Female patients must be postmenopausal, surgically sterile or they must agree to use acceptable methods of birth control (i.e., a hormonal contraceptive with barrier method, intra-uterine device, diaphragm with spermicidal or condom with spermicide, abstinence) for the duration of the study and for one month following study completion. Female patients with childbearing potential must have a negative serum pregnancy test within 10 days before the first study drug administration. Male patients must be surgically sterile or agree to use an acceptable method of contraception.

12. Concurrent, active second malignancy for which the patient is receiving therapy, excluding basal cell carcinoma of the skin or carcinoma in situ of the cervix.

13. Any medical conditions that, in the Investigator's opinion, would impose excessive risk to the patient. Examples of such conditions include infection requiring parenteral anti-infective treatment, hydronephrosis, liver failure, any altered mental status or any psychiatric condition that would interfere with the understanding of the informed consent.

14. Unwilling or unable to comply with procedures required in this protocol.

Length of Study

Stable and responding patients were treated in this investigation as long as he/she has evidence of clinical benefit (stable disease or a response) in the absence of unacceptable adverse events. Study closure was planned 12 months after the last patient is accrued.

Investigational Products/Dose/Route/Regimen

Plinabulin or Placebo:

The initial dose of plinabulin was 30 mg/m$^2$ or 20 mg/m$^2$. Dose adjustments depended on observed adverse events. Volume of administration varied based on assigned dose and patient body surface area. The clinical formulation were supplied as a concentrated solution in 40% Solutol® HS-15/60% propylene glycol in amber vials containing 80 mg of drug in 20 mL (4 mg/mL) and were stored at room temperature. Each vial was designated for single use. The correct volume of drug (at a concentration of 4 mg/mL in the vial) was diluted in dextrose 5% in water (D5W) at a dilution of 1:20 and administered IV peripherally or centrally. Infusion time may be increased as clinically indicated at the direction of the Sponsor. Plinabulin and placebo must be protected from light at all times including storage, dilution and administration. Plinabulin and placebo should be administered within 6 hours of dilution.

Premedication with anti-emetics (including significant anti-emetic regimens such as substance P inhibitor, corticosteroid and/or dopamine antagonist combinations) per institutional practice should be provided before each dose of plinabulin or placebo. 5-HT$^3$ antagonists should not be routinely administered subsequent to or between doses of plinabulin or placebo unless clearly necessary. Patients should receive a motility enhancing agent such as metaclopromide as part of their antiemetic regimen.

Bowel motility should be maintained per institutional practice as used for drugs such as vincristine, including use of agents such as stool softeners, bulking agents, stimulating agents and/or dopamine antagonists, as well as minimizing use of motility reducing agents such as opiates to when clearly indicated or managing opiate induced constipation with agents such as methylnaltrexone as indicated. If significant constipation develops, it should be managed immediately and plinabulin or placebo administration should be delayed until resolution. Careful observance for signs of ileus and early diagnostic evaluation with radiographic and/or ultrasound studies is recommended.

If a >20% increase in systolic blood pressure is observed after administration of plinabulin or placebo, oral amlodipine 10 mg or an equivalent calcium channel blocker should be administered one hour before each subsequent dose. Increases in systolic blood pressure above 180 mmHg should be managed with nitroprusside or similar regimen per institutional practice.

Docetaxel:

The initial dose of docetaxel was 75 mg/m$^2$. Dose adjustments depended on observed adverse events.

Volume of administration varied based on assigned dose and patient body surface area.

As a standard approved and commercially available chemotherapy agent, the investigator and study site staff should be experienced in the use of docetaxel and familiar with the formulation and docetaxel prescribing information provided by the manufacturer.

Docetaxel should be obtained from the institutional pharmacy and prepared per institutional protocol. Administration should be carried out with a 1 hour IV infusion per institutional protocol at the dose prescribed by this clinical trial protocol.

Oral dexamethasone (16 mg) was given the day prior to, the day of and the day following docetaxel infusion (Day 1). A similar corticosteroid premedication regimen may be used in accordance with local institutional practices. The dose of dexamethasone or other corticosteroid should be appropriately reduced for patients already utilizing corticosteroids.

Procedures

Screen:

(within 28 days prior to start of treatment (i.e., Day −28 to 1)) Informed consent, medical history and concomitant medications; ECG, radiographic tumor assessments and tumor markers as appropriate.

Baseline Assessments:

(within 14 days of start of treatment, i.e., day −14 to 1) Physical examination, vital signs, ECOG performance status, concomitant medication usage, safety laboratory tests. Women of childbearing potential must have a negative serum pregnancy test within 10 days of start of treatment. If there was any history or findings suggestive of significant heart disease, a cardiology consultation should be obtained.

Treatment Phase:

Safety assessments (including a complete physical examination) were performed prior to study drug infusion. Safety assessments (including complete physical examination) were performed prior to each subsequent cycle (2+). Additionally, the following were evaluated:

CBC with differential/platelets and clinical chemistry were performed up to 72 hours prior to Day 1 of each cycle; an additional assessment occurred in Cycle 1/Day 15.

Vital signs (heart rate, respiratory rate, blood pressure and temperature) were taken on the days of infusion immediately before and after each study drug infusion and at 30 and 60 minutes following last infusion on the first cycle. During subsequent cycles, vitals were taken prior to and after each infusion during the physical examination.

Assessment of response to treatment occurred during the rest period of the second cycle (and approximately every 2 cycles thereafter).

Treatment continued until there was evidence of progressive disease, unacceptable treatment-related adverse events, the study is closed,—or the patient is withdrawn from the study (either due to withdrawal of consent or Investigator judgment).

End-of Study (Off Study) Visit:

All patients receiving at least one dose of study drug and discontinuing treatment for any reason except death completed this assessment, within 28 days of the last study drug administration. Patients underwent physical examination, vital signs, body weight, documentation of ECOG performance status, and routine lab tests including a pregnancy test will be drawn.

Follow-Up Visits:

Follow-up visits were required to monitor ongoing drug-related adverse events and survival. Patients with drug related adverse events of Grade >=2 observed at the End of Study assessment, should be followed-up monthly until the adverse event has resolved to Grade <1 or the event is believed to be chronic or patient received other anti-cancer therapy. Follow-up for survival should occur at 3-month intervals.

Assessments of:

Efficacy:

Comparisons were made of efficacy endpoints between Arm D and Arm DN. The primary efficacy endpoint is overall survival. Secondary endpoints include response rate, duration of response, quality of life, neutropenia rate and G-CSF usage.

Safety:

Adverse events spontaneously declared by the patients or noted during physical examination, vital signs, ECOG performance status and laboratory tests.

Statistical Analyses

Efficacy:

The distributions of overall survival and any other time-to-event endpoints were summarized using the Kaplan-Meier method. The log-rank test was used to compare the efficacy endpoints between treatment groups. All statistical tests were carried out using one-sided tests at the 5% level of significance. The primary objective of this trial is to assess the effect of the addition of plinabulin on overall survival.

Safety:

All patients were evaluated for safety analysis if they received at least one dose of study drug. The safety data were presented by study arm in individual listings and summary tables, including frequency tables for adverse events and frequency and shift tables for laboratory variables.

Results:

1) Neutropenia is Reduced in the Combination of Plinabulin and Docetaxel Group

The tolerability profile for plinabulin when added to docetaxel is better than docetaxel alone. Due to unbearable docetaxel side effects, the initial dose of 75 mg/m$^2$ docetaxel was decreased in 10% of patients (5 of 50) in the plinabulin 30 mg/m$^2$ plus docetaxel treatment arm whereas, the percent in the matched docetaxel alone arm was much higher at 18.2% of patients (10 of 55). In plinabulin 20 mg/m$^2$ cohort, the same result was seen, in which a lower proportion of patients required docetaxel dose reductions when treated with the combination (2.5%) than the companion D arms (22.2%).

There was a lower incidence of neutropenia in patients in the DN 30 mg/m$^2$ arm compared with its companion D arm (8.0% versus 36.4%, p<0.001) and the DN 20 mg/m$^2$ arm compared with its companion D arm (7.5% versus 22.2%). The DN 30 mg/m$^2$ arm (n=50) had a significantly lower incidence of all grades of neutropenia, especially ≥Grade 3 neutropenia compared with the pooled D arm (n=73) at 8.0% versus 27.4%, respectively (p=0.010). Similar results were observed for the 20 mg/m$^2$ arm (5.0% versus 27.4%, respectively; p=0.050). The neutropenia reduction effect is shown in FIG. 5. The proportion of patients who required G-CSF and the rate of docetaxel dose reduction were also lower in both DN arms compared with the D arms. The G-CSF use percentage decrease in combined DN arm vs. combined D arm is statistically significant at 0.0013%.

TABLE 9

Comparison of Docetaxel dose redution, neutropenia rate and G-CSF use in DN Arm and D Arm

| | 30 mg/m$^2$ Cohort | | 20 mg/m$^2$ Cohort | |
|---|---|---|---|---|
| | DN arm N = 50 | D arm N = 55 | DN arm N = 40 | D arm N = 18 |
| Docetaxel dose reductions (n [%]) | 5 (10.0%) | 10 (18.2%) | 1 (2.5%) | 4 (22.2%) |
| Neutropenia (Grade 3, 4) | 8.0% (p = 0.01) | 27.4% | 5% (p = 0.05) | 27.4% |
| G-CSF use (n [%]) | 7 (14%) | 16 (29.1%) | 2 (5%) | 6 (33.3%) |

Abbreviations:
D = docetaxel;
DN = docetaxel + plinabulin;
G-CSF = granulocyte colony stimulating factor.
Note:
G-CSF included the following concomitant medications: pegfilgrastim, filgrastim, neupogen, neulasta 2) Large Tumor Patient Population Overall Survival (OS) Benefit from Plinabulin and Docetaxel Combination In the above study, comparing plinabulin (30 mg/m$^2$, Day 1 and Day 8 of each 21-day cycle) plus docetaxel (75 mg/m$^2$, Day 1 of each cycle) with docetaxel alone in patients with locally advanced or metastatic NSCLC who had failed at least 1 prior chemotherapy regimen, in the 30 mg/m$^2$ group there was no significant difference between the plinabulin plus docetaxel treatment group (OS=8.7 M (month)) compared to the docetaxel control treatment group (OS=7.5 M) in OS (Table 11, FIG. 6), progression-free survival [PFS], and response rate. The inventor then performed extensive analyses of the data to identify a subgroup which react to the plinabulin and docetaxel combination.

Of the subgroup analyses, there is a clear division of OS at tumor size of 3 cm: in the group of at least 1 tumor >3 cm, >5 cm, or >7 cm, there was a clear OS benefit in the DN Arm compared with the D Arm, but in all tumor <3 cm group, there was no OS difference in (6.45 M vs. 6.47 M, Table 11 FIG. 6). The larger the tumor size, the more significant the OS benefit, hazard ratio, and response rate in the combination group compared with the docetaxel group alone (Table 11, FIG. 6).

Thus the investor has discovered a uniquely defined large tumor group which benefit from the optimum plinabulin and docetaxel combination, which was never reported before in any literature.

TABLE 10

Comparison of OS and Response Rate in Arm DN (30 mg/m$^2$) and Arm D at various size of the largest primary tumor

| Treatment Group | All Patients | | ≤3 cm | | >3 cm | | >5 cm | | >7 cm | |
|---|---|---|---|---|---|---|---|---|---|---|
| | DN | D | DN | D | DN | D | DN | D | DN | D |
| OS (month) | 8.7 | 7.5 | 6.5 | 6.5 | 9.0 | 7.5 | 9.0 | 6.7 | 7.32 | 5.03 |
| Response Rate (%) | 14 | 14.5 | 12.5 | 15.8 | 14.7 | 13.9 | 20 | 15 | 25 | 20 |
| Hazard Ratio | 0.972 | | 0.934 | | 0.967 | | 0.750 | | 0.507 | |

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method of treating a grade 3 or 4 neutropenia in a subject being administered 75 mg/m$^2$ docetaxel, comprising administering plinabulin at a dose of 20 mg/m$^2$ or 30 mg/m$^2$ to the subject within 0.5 h and 72 h after administering the docetaxel.

2. The method of claim 1, wherein said administering results in a neutropenia rate lower than that induced by docetaxel alone.

3. The method of claim 1, wherein the plinabulin administration is about 1 to 24 hours after the docetaxel administration.

4. The method of claim 3, wherein plinabulin is administered about 2 hours after the administration of the docetaxel.

5. The method of claim 1, wherein the docetaxel-induced neutropenia rate is reduced by at least 4% for grade 3 neutropenia.

6. The method of claim 1, wherein the docetaxel-induced neutropenia rate is reduced by at least 15% for grade 4 neutropenia.

* * * * *

UNITED STATES PATENT AND TRADEMARK OFFICE
CERTIFICATE OF CORRECTION

PATENT NO. : 10,596,169 B2
APPLICATION NO. : 15/028376
DATED : March 24, 2020
INVENTOR(S) : Lan Huang It is certified that error appears in the above-identified patent and that said Letters Patent is hereby corrected as shown below:

On the Title Page

Column 1, Item (56), Line 3, under Foreign Patent Documents, delete "2014160183" and insert --2014/160183--.

In the Specification

In Column 1, Line 47, delete "alkyloids," and insert --alkaloids,--.

In Column 3, Line 9, delete "plinabulin" and insert --plinabulin.--.

In Column 3, Line 57, delete "Docetaxel)" and insert --Docetaxel).--.

In Column 4, Lines 48-49, delete "(1,1dimethyethyl)" and insert --(1,1-dimethyethyl)--.

In Column 4, Line 50, delete "(3Z,6Z)]" and insert --(3Z,6Z)--.

In Column 4, Line 57, delete "vascularture," and insert --vasculature,--.

In Column 4, Line 63, delete "injection" and insert --injection.--.

In Column 5, Line 35, delete "Plinubulin" and insert --Plinabulin--.

In Column 8, Line 10, delete "mice" and insert --mice.--.

In Column 9, Line 43 (Approx.), delete "(24" and insert --24--.

In Columns 11-12, Table 2, Line 4 (Approx.), delete "% CHANG" and insert --% CHANGE--.

In Column 15, Line 21, delete "administration" and insert --administration.--.

Signed and Sealed this
Thirty-first Day of May, 2022

Katherine Kelly Vidal
*Director of the United States Patent and Trademark Office*

CERTIFICATE OF CORRECTION (continued)
U.S. Pat. No. 10,596,169 B2

In Column 23, Line 5, delete "patients" and insert --patients.--.

In Column 23, Line 57, delete "AST<2.5" and insert --AST≤2.5--.

In Column 23, Line 57, delete "(<1.5" and insert --(≤1.5--.

In Column 24, Line 3, delete "<1." and insert --≤1.--.

In Column 24, Line 11 (Approx.), delete "<2." and insert --≤2.--.

In Column 24, Line 16 (Approx.), delete "<ULN" and insert --≤ULN--.

In Column 24, Line 17, delete "ALT<2.5" and insert --ALT≤2.5--.

In Column 25, Lines 58-59, delete "metaclopromide" and insert --metoclopramide--.

In Column 28, Table 9, Line 1, delete "redution," and insert --reduction,--.

In Column 28, Line 58, delete "<3" and insert --≤3--.